(12) United States Patent
Kurokawa et al.

(10) Patent No.: US 10,219,762 B2
(45) Date of Patent: Mar. 5, 2019

(54) X-RAY CT DEVICE AND IMAGING METHOD FOR X-RAY CT IMAGES

(71) Applicant: HITACHI, LTD., Tokyo (JP)

(72) Inventors: Shinji Kurokawa, Tokyo (JP); Yushi Tsubota, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 220 days.

(21) Appl. No.: 15/323,980

(22) PCT Filed: Jun. 22, 2015

(86) PCT No.: PCT/JP2015/067891
§ 371 (c)(1),
(2) Date: Jan. 5, 2017

(87) PCT Pub. No.: WO2016/009787
PCT Pub. Date: Jan. 21, 2016

(65) Prior Publication Data
US 2017/0202527 A1  Jul. 20, 2017

(30) Foreign Application Priority Data

Jul. 18, 2014 (JP) ................................ 2014-148246

(51) Int. Cl.
*A61B 6/00* (2006.01)
*A61B 6/03* (2006.01)
*A61B 6/04* (2006.01)

(52) U.S. Cl.
CPC ............ *A61B 6/4021* (2013.01); *A61B 6/032* (2013.01); *A61B 6/0407* (2013.01);
(Continued)

(58) Field of Classification Search
CPC ............................. A61B 6/032; A61B 6/4021
See application file for complete search history.

(56) References Cited

U.S. PATENT DOCUMENTS

| 4,637,040 A | 1/1987 | Sohval et al. |
| 5,173,852 A | 12/1992 | Lonn |
| (Continued) | | |

FOREIGN PATENT DOCUMENTS

| JP | 60-106439 A | 6/1985 |
| JP | 4-231940 A | 8/1992 |
| (Continued) | | |

OTHER PUBLICATIONS

Marc Kachelriess et al., "Flying Focal Sport (FFS) in Cone-Beam CT", IEEE Transactions on Nuclear Science, Jun. 2006, pp. 1238-1247, vol. 53. No. 3.

(Continued)

*Primary Examiner* — Dani Fox
(74) *Attorney, Agent, or Firm* — Mattingly & Malur, PC

(57) ABSTRACT

An X-ray CT device which improves resolution in a peripheral region distant from a rotation center. According to an FFS method of moving an X-ray focal point, a gap width of projection positions on an X-ray detector of a first X-ray trajectory from the X-ray focal point of a first view and a second X-ray trajectory from the X-ray focal point of a second view is obtained. A position of the X-ray focal point of the first and second views is set so that a gap width 15 of the projection positions on the X-ray detector of the first X-ray trajectory and the second X-ray trajectory which pass through a point within a predetermined first region close to the X-ray focal point from the rotation center is closer to (N−½) times (N=any one of 1, 2, 3, . . . ) of a width of a channel of the X-ray detector.

11 Claims, 23 Drawing Sheets

(52) U.S. Cl.
CPC ............ *A61B 6/4429* (2013.01); *A61B 6/461* (2013.01); *A61B 6/5205* (2013.01); *A61B 6/54* (2013.01); *A61B 6/42* (2013.01); *A61B 6/467* (2013.01); *A61B 6/5258* (2013.01)

(56) References Cited

U.S. PATENT DOCUMENTS

| | | |
|---|---|---|
| 5,590,164 A | 12/1996 | Kawai et al. |
| 6,272,199 B1 | 8/2001 | Sembritzki et al. |
| 7,570,730 B2 | 8/2009 | Kohler et al. |
| 8,792,610 B2 | 7/2014 | Miyazaki |
| 2008/0095299 A1 | 4/2008 | Kohler et al. |
| 2010/0034344 A1 | 2/2010 | Hein et al. |
| 2011/0243298 A1 | 10/2011 | Miyazaki |

FOREIGN PATENT DOCUMENTS

| | | |
|---|---|---|
| JP | 8-010251 A | 1/1996 |
| JP | 2000-083942 A | 3/2000 |
| JP | 2000-139893 A | 5/2000 |
| JP | 2007-529258 A | 10/2007 |
| JP | 2010-035812 A | 2/2010 |
| JP | 2011-229906 A | 11/2011 |

OTHER PUBLICATIONS

International Search Report of PCT/JP2015/067891 dated Sep. 15, 2015.

International Preliminary Report on Patentability received in corresponding International Application No. PCT/JP2015/067891 dated Feb. 2, 2017.

| View | 1 | 2 | 3 | 4 | 5 |
|---|---|---|---|---|---|
| FOCAL MOVEMENT | ABSENT | PRESENT | ABSENT | PRESENT | ABSENT |
| MOVEMENT AMOUNT (ch) OF PROJECTION POSITION OF POINT WITHIN FIRST REGION | 0 | −1.5 | −2 | −3.5 | −4 |
| MOVEMENT AMOUNT (ch) OF PROJECTION POSITION OF POINT WITHIN SECOND REGION | 0 | 0.5 | 1.5 | 2 | 3 |

| View | 1 | 2 | 3 | 4 | 5 | 6 | 7 | 8 |
|---|---|---|---|---|---|---|---|---|
| GAP WIDTH $\Delta ch1$ (ch) IN CASE OF NO FOCAL MOVEMENT | 0 | -1.1 | -1.1 | -1.1 | -1.1 | -1.1 | -1.1 | -1.1 |
| MOVEMENT AMOUNT (ACCUMULATION OF $\Delta ch1$) (ch) IN CASE OF NO FOCAL MOVEMENT | 0 | -1.1 | -2.2 | -3.3 | -4.4 | -5.5 | -6.6 | -7.7 |
| GAP WIDTH $\Delta ch1'$ (ch) IN CASE OF FOCAL MOVEMENT | 0 | -1.5 | -0.5 | -1.5 | -0.5 | -1.5 | -1.5 | -0.5 |
| FOCAL MOVEMENT DISTANCE $\Delta S$ | 0 | $\Delta S$ 1-2 | $\Delta S$ 1-3 | $\Delta S$ 1-4 | $\Delta S$ 1-5 | $\Delta S$ 1-6 | $\Delta S$ 1-7 | $\Delta S$ 1-8 |
| MOVEMENT AMOUNT CHANGE ($\Delta ch1' - \Delta ch$) (ch) CAUSED BY FOCAL MOVEMENT | 0 | -0.4 | +0.2 | -0.2 | +0.4 | 0 | -0.4 | +0.2 |
| MOVEMENT AMOUNT (ACCUMULATION OF $\Delta ch1'$) (ch) IN CASE OF FOCAL MOVEMENT | 0 | -1.5 | -2 | -3.5 | -4 | -5.5 | -7 | -7.5 |

FIG. 16

| View | 1 | 2 | 3 | 4 |
|---|---|---|---|---|
| GAP WIDTH $\Delta ch1$ (ch) IN CASE OF NO FOCAL MOVEMENT | 0 | −1.1 | −1.1 | −1.1 |
| MOVEMENT AMOUNT (ACCUMULATION OF $\Delta ch1$) (ch) IN CASE OF NO FOCAL MOVEMENT | 0 | −1.1 | −2.2 | −3.3 |
| GAP WIDTH $\Delta ch1'$ (ch) IN CASE OF FOCAL MOVEMENT | 0 | −1.5 | −0.7 | −1.5 |
| FOCAL MOVEMENT DISTANCE $\Delta S1$ | 0 | $\Delta S1$-2 | $\Delta S1$-3 | $\Delta S1$-4 |
| MOVEMENT AMOUNT CHANGE ($\Delta ch1' - \Delta ch$) (ch) CAUSED BY FOCAL MOVEMENT | 0 | −0.4 | +0.4 | −0.4 |
| MOVEMENT AMOUNT (ACCUMULATION OF $\Delta ch1'$) (ch) IN CASE OF FOCAL MOVEMENT | 0 | −1.5 | −2.2 | −3.7 |

FIG. 17

| View | 1 | 2 | 3 | 4 |
|---|---|---|---|---|
| GAP WIDTH $\Delta ch1$ (ch) IN CASE OF NO FOCAL MOVEMENT | 0 | -1.1 | -1.1 | -1.1 |
| MOVEMENT AMOUNT (ACCUMULATION OF $\Delta ch1$) (ch) IN CASE OF NO FOCAL MOVEMENT | 0 | -1.1 | -2.2 | -3.3 |
| GAP WIDTH $\Delta ch1'$ (ch) IN CASE OF FOCAL MOVEMENT | 0 | -1.6 | -1.1 | -1.6 |
| FOCAL MOVEMENT DISTANCE $\Delta S1$ | 0 | $\Delta S$ 1-2 | $\Delta S$ 1-3 | $\Delta S$ 1-4 |
| MOVEMENT AMOUNT CHANGE ($\Delta ch1' - \Delta ch$) (ch) CAUSED BY FOCAL MOVEMENT | 0 | -0.5 | 0 | -0.5 |
| MOVEMENT AMOUNT (ACCUMULATION OF $\Delta ch1'$) (ch) IN CASE OF FOCAL MOVEMENT | 0 | -1.6 | -2.2 | -3.8 |

FIG. 18

X-RAY CT DEVICE AND IMAGING METHOD FOR X-RAY CT IMAGES

TECHNICAL FIELD

The present invention relates to an X-ray CT device, and particularly relates to a technique for improving measurement accuracy of a subject by improving spatial resolution.

BACKGROUND ART

An X-ray computed tomography (CT) device computationally reconstructs a tomographic image (hereinafter, referred to as a CT image) of a subject by imaging X-ray transmission data of the subject while rotating an X-ray source and a pair of X-ray detectors (hereinafter, referred to as a scanner) which are disposed to face each other across the subject. The X-ray CT device is widely used in the field of industrial and security-purpose inspection devices or medical image diagnostic devices. In the field of a medical X-ray CT device, in recent years, the X-ray detector has occupied the larger area, and a scanner has been rotated faster. Accordingly, a wide imaging region can be measured in a short period of time. In addition, the faster rotation speed of the scanner improves time resolution. As a result, measurement accuracy is significantly improved for a moving subject such as the heart and coronary arteries. In accordance with the highly improved accuracy in X-ray CT measurement, there is a growing need for improved spatial resolution. For example, there is a need for following up whether or not a restenosis appears or a plaque status, through the inside of a stent inserted into a stenosed blood vessel in order to dilate the stenosed blood vessel. High spatial resolution is required in order to inspect a microstructure of the subject.

In order to improve the spatial resolution for measurement using the X-ray CT device, a detection element of the X-ray detector normally needs to be miniaturized, that is, a size thereof needs to be reduced. However, in a case where X-ray doses incident on the X-ray detector are the same as each other, if the detection element is miniaturized, the number of X-ray photons incident on one detection element decreases. Accordingly, an signal-to-noise ratio of a detection signal is degraded. In order to improve the signal-to-noise ratio, it is necessary to increase the X-ray doses. However, in a case of medical measurement, an increase in the X-ray doses results in an increase in X-ray exposures of a subject to be tested. For the above-described reason, the size of the detection element of the X-ray detector is determined by the trade-off between the spatial resolution and the X-ray exposure amount. A medical X-ray CT device normally employs an X-ray element having an X-ray input surface whose size is approximately 1 mm square.

On the other hand, as a method of improving the spatial resolution (or decreasing artifacts) without reducing the size of the detection element of the X-ray detector, a method calling a flying focal spot (FFS) method has been proposed (refer to NPL 1). According to the FFS method, positions of X-ray focal points of adjacent views are shifted from each other so that an X-ray trajectory extending from an X-ray focal point to each X-ray detection element of the X-ray detector and an X-ray trajectory of the adjacent view are shifted in the X-ray detector coordinate system. According to NPL 1, this configuration improves the resolution mainly at a rotation center.

PTL 1 discloses a configuration in which the positions of the X-ray focal points are shifted so that the positions of the X-ray focal points are the same as each other in the adjacent views. In this manner, each of the X-ray trajectories of a certain view exactly pass (interlaces) through gaps of the X-ray trajectories of the adjacent view. In this manner, a relationship is established so that the X-ray trajectories of the adjacent views completely interlace with each other not only at the rotation center but also in all imaging regions. Therefore, the resolution is also improved in the region in addition to the rotation center.

CITATION LIST

Patent Literature

[PTL 1] JP-A-2010-35812

Non Patent Literature

[NPL 1] Marc Kachelriess, Michael Knaup, Christian Penssel, and Willi A. Kalender, "Flying Focal Spot (FFS) in Cone-Beam CT", IEEE TRANSACTIONS ON NUCLEAR SCIENCE, VOL. 53, NO. 3, pp. 1238 to 1247, JUNE 2006

SUMMARY OF INVENTION

Technical Problem

In a case of the CT image, it is known that the resolution of a peripheral region tends to become lower than that of the rotation center. However, the FFS technique in NPL 1 is a technique for improving the resolution at the rotation center of the CT image, and it is difficult to improve the resolution (or to decrease the artifacts) in the peripheral region.

In addition, according to a method of overlapping the positions of the X-ray focal points of the adjacent views as in PTL 1, it is not possible to overlap the X-ray focal points of all views at one location. Accordingly, it is necessary to overlap the X-ray focal points by pairing every two views. If the X-ray focal points overlap each other by pairing every two views in this way, it means that the effective number of views is reduced by half. In some cases, the resolution cannot necessarily be improved. In addition, when the X-ray trajectories of two views are completely interlaced with each other (shifted as far as exactly ½ of the gap of the X-ray trajectory), limitations are imposed on not only a shifted distance of the X-ray focal points but also the number of views. The number of views which is larger than and next to the number of 1,926 views are calculated as 5,777 that is extremely large number. Consequently, if the technique disclosed in PTL 1 is applied to an actual X-ray CT device, there are some difficulties.

An object of the present invention is to provide an X-ray CT device which can improve resolution in a peripheral region distant from a rotation center.

Solution to Problem

In order to achieve the above-described object, an X-ray CT device according to the present invention includes an X-ray tube provided with capability to move an X-ray focal point, an X-ray detector, a table which disposes a subject between the X-ray tube and the X-ray detector, a rotary plate that is mounted with the X-ray tube and the X-ray detector so as to rotate the X-ray tube and the X-ray detector around the subject, a reconstruction processing unit that reconstructs an image by incorporating a detection result of the X-ray detector with regard to multiple views corresponding to a rotation angle of the rotary plate, and a focus control unit that sets a position of the X-ray focal point of the X-ray tube for each of the views. First X-ray trajectories are X-ray trajectories reaching each of multiple X-ray detectors from the X-ray focal point in a predetermined first view out of the multiple views. Second X-ray trajectories are X-ray trajectories reaching each of X-ray detectors from the X-ray focal point in a second view adjacent to the first view. The focus control unit sets a position of each X-ray focal point of the first view and the second view so that a gap width of projection positions on the X-ray detector of the first X-ray trajectory and the second X-ray trajectory which respectively pass through the same point of the subject within a predetermined region different from a rotation center of the rotary plate is closer to (N−½) times (N=any one of 1, 2, 3, . . . ) of the channel width of the X-ray detector, compared to a gap width of projection positions on the X-ray detector of the first X-ray trajectory and the second X-ray trajectory which respectively pass through the rotation center of the rotary plate.

Advantageous Effects of Invention

According to the present invention, it is possible to improve resolution (or to decrease artifacts) in a peripheral region distant from a rotation center.

BRIEF DESCRIPTION OF DRAWINGS

FIG. 16 is a view using a tabular format for describing a gap width Δch1 of the projection position without focus shift, a gap width Δch1' of the projection position with focus shift, and a focal movement distance ΔS1, in each view according to the fifth embodiment.

FIG. 17 is a view using a tabular format for describing the gap width Δch1 of the projection position without focus shift, the gap width Δch1' of the projection position with focus shift, and the focal movement distance ΔS1, in each view according to a sixth embodiment.

FIG. 18 is a view using a tabular format for describing the gap width Δch1 of the projection position without focus shift, the gap width Δch1' of the projection position with focus shift, and the focal movement distance ΔS1, in each view according to a seventh embodiment.

FIGS. 20(a) and 20 (b) are views for describing an example of setting the predetermined distance R for each portion of an imaging target according to a ninth embodiment.

DESCRIPTION OF EMBODIMENTS

Embodiments according to the present invention will be described with reference to the drawings.

First Embodiment

Figure 1:
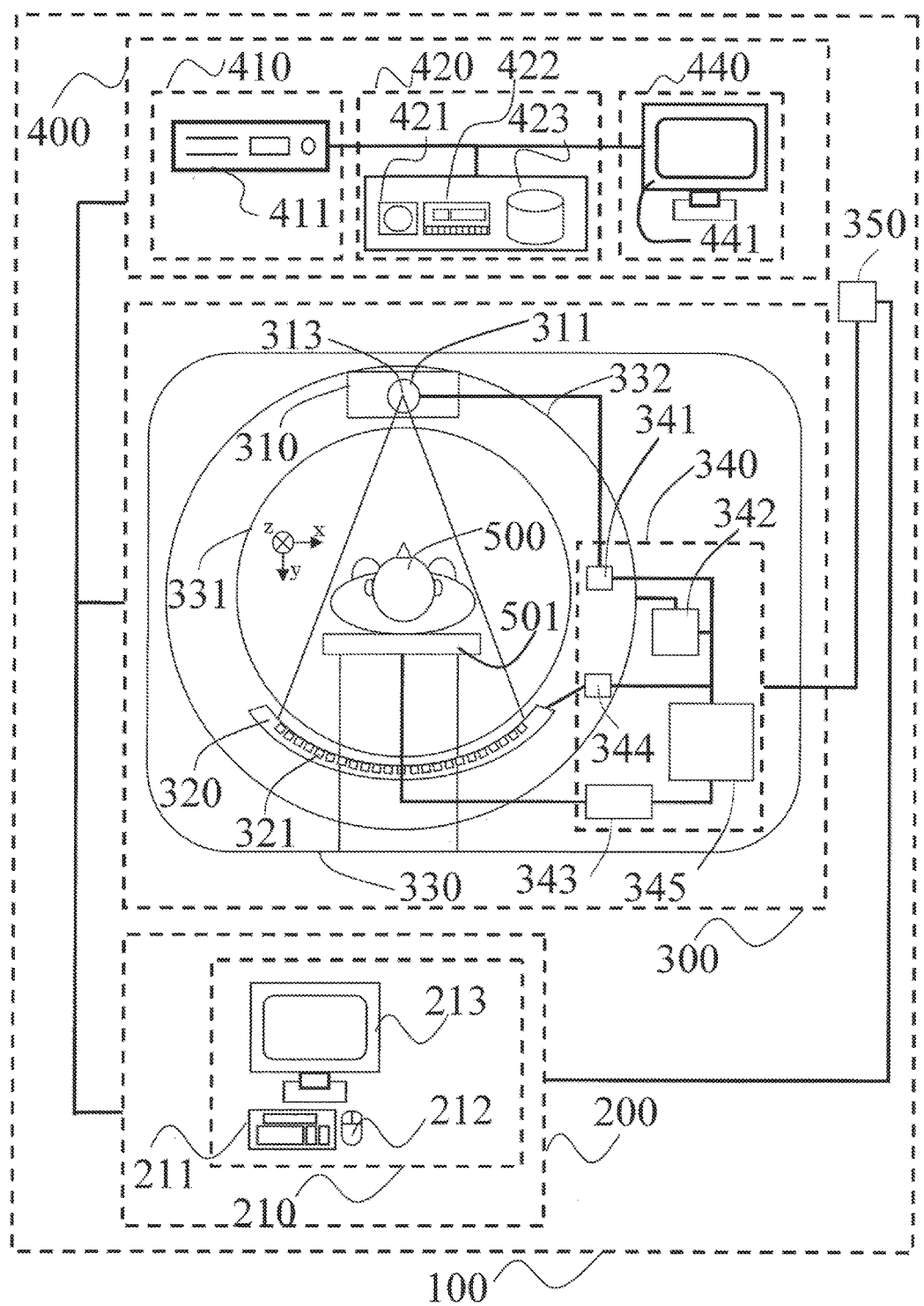
FIG. 1 is a block diagram illustrating an overall configuration of an X-ray CT device according to a first embodiment.

As illustrated in FIG. 1, an X-ray CT device according to a first embodiment of the present invention has an X-ray tube 311 provide with capability to move an X-ray focal point, an X-ray detector 320, a table 501 for disposing a subject 500 between the X-ray tube 311 and the X-ray detector 320, a rotary frame 332 that is mounted with the X-ray tube 311 and the X-ray detector 320 so as to rotate the X-ray tube 311 and the X-ray detector 320 around the subject 500, a reconstruction processing unit 420 that reconstructs an image by incorporating a detection result of the X-ray detector 320 with regard to multiple views corresponding to a rotation angle of the rotary plate 332, and a focus control unit 350 that sets a position of the X-ray focal point of the X-ray tube 311 for each of the views. The X-ray detector 320 includes multiple channels 321 which are arrayed along a rotation direction of the rotary plate 332.

Figure 2:
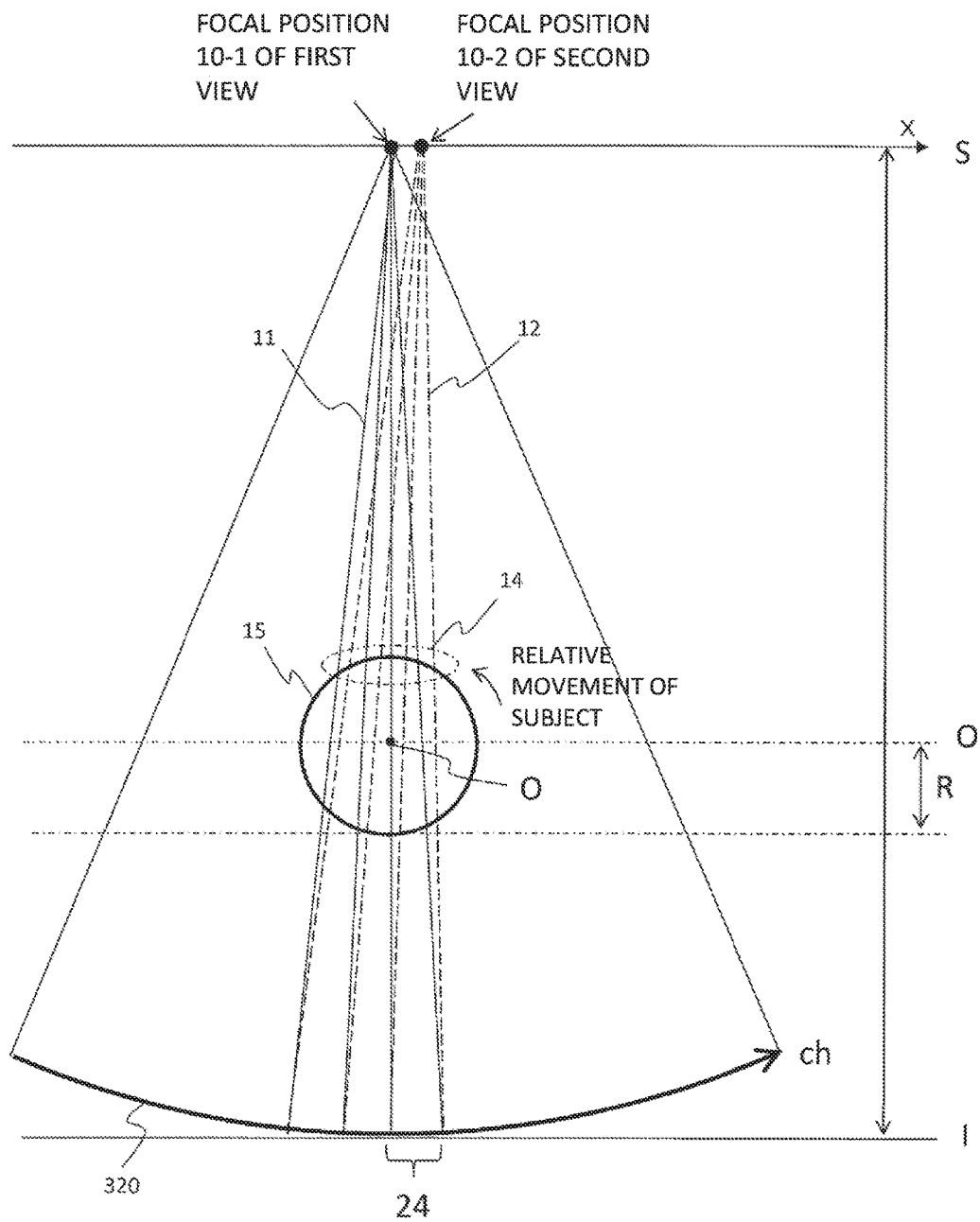
FIG. 2 is a view for describing X-ray trajectories 11 and 12 according to the first embodiment, in a coordinate system fixed to an X-ray detector of a rotary plate.
Figure 3:
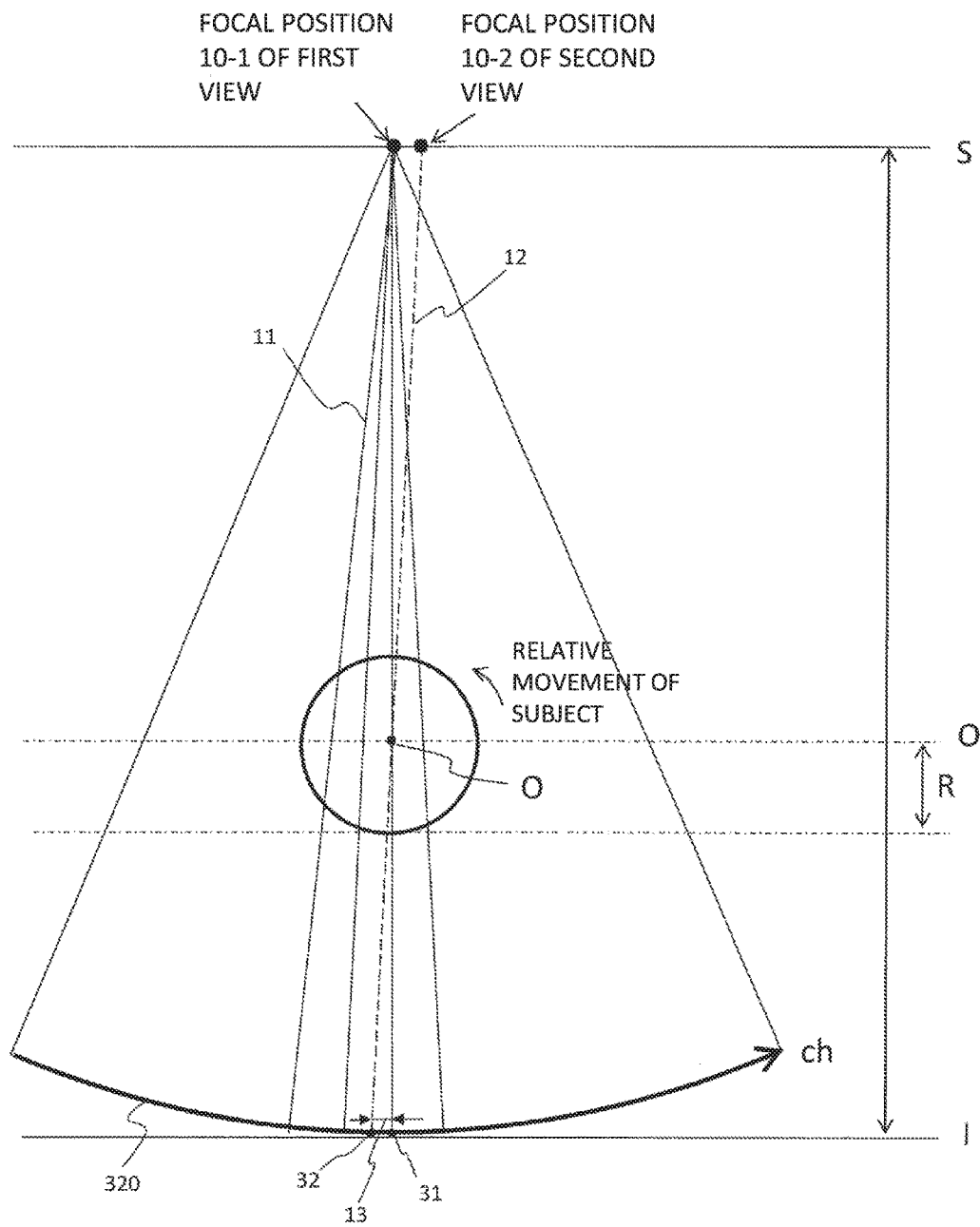
FIG. 3 is a view for describing a gap width 13 in an X-ray detector 320 of the X-ray trajectories 11 and 12 which pass through a rotation center O, in the coordinate system fixed to the X-ray detector of the rotary plate.
Figure 4:
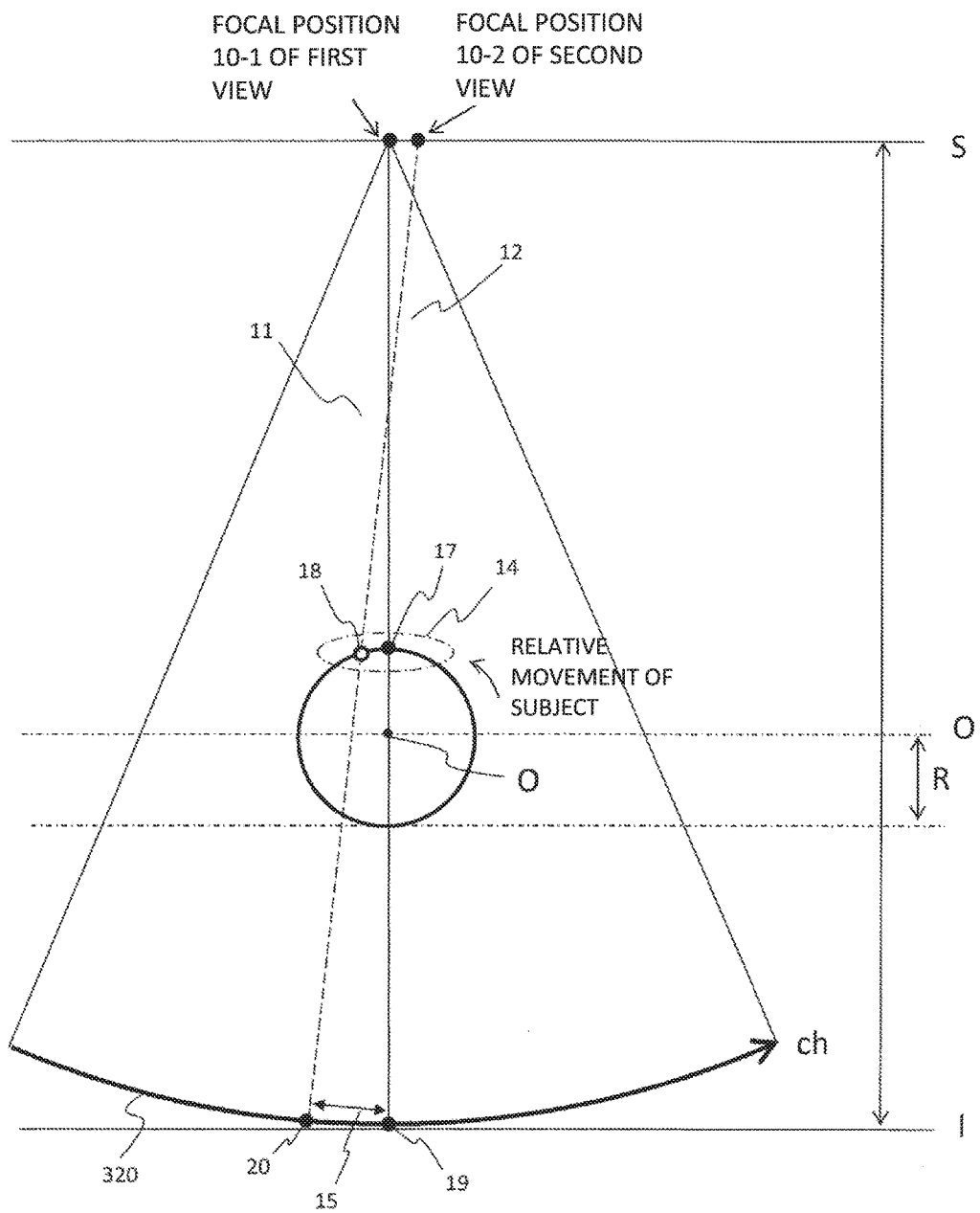
FIG. 4 is a view for describing a gap width 15 in the X-ray detector 320 of the X-ray trajectories 11 and 12 which pass through the same point 17 (18) within a first region 14, in the coordinate system fixed to the X-ray detector of the rotary plate.

The focus control unit 350 sets a position of an X-ray focal point 10 for each of the views so as to satisfy the following condition. FIGS. 2 to 4 illustrate X-ray trajectories in a coordinate system fixed to the X-ray detector 320 of the rotary plate 332. As illustrated in FIG. 2, X-ray trajectories reaching the X-ray detector 320 from an X-ray focal point 10-1 in a first view out of the multiple views are set to a first X-ray trajectory 11. X-ray trajectories reaching the X-ray detector 320 from an X-ray focal point 10-2 in a second view subsequent to the first view are set to second X-ray trajectories 12. As illustrated in FIG. 3, a gap width of projection positions on the X-ray detector 320 of the first X-ray trajectory 11 and the second X-ray trajectory 12 which respectively pass through a rotation center O of the rotary plate 332 represents a gap width 13. As illustrated in FIG. 4, the focus control unit 350 sets a focal position 10-1 of the first view and a focal position 10-2 of the second view so that a gap width 15 of the projection positions on the X-ray detector 320 of the first X-ray trajectory 11 and the second X-ray trajectory 12 which respectively pass through the same point 17 (18) of the subject 500 within a predetermined first region 14 different from the rotation center O is closer to (N−½) times (N=any one of 1, 2, 3, . . . ) of a width 24 of a channel 321 of the X-ray detector 320, compared to the above-described gap width 13 of the first and second X-ray trajectories which pass through the rotation center O.

In this manner, with regard to a point of the subject within the first region 14, the first and second X-ray trajectories have an interlaced relationship. Accordingly, it is possible to satisfy a condition for improving resolution of an X-ray CT image in the first region 14 distant from the rotation center O.

In FIG. 4, a point 18 of the subject 500 in the second view is the same point as a point 17 of the subject 500 in the first view. In an actual space, the rotary plate 331 is rotated around the subject 500. Accordingly, in the coordinate system in FIGS. 2 to 4, which is fixed to the X-ray detector 320 of the rotary plate 332, the point 17 is rotated and moved relative to the rotary plate 331, and is located at the point 18 in the second view.

The first embodiment will be further described. In the first view in FIG. 4, a position where the X-ray (first X-ray trajectory 11) which passes through the point 17 of the subject 500 within the predetermined first region 14 distant from the rotation center O of the subject 500 is incident on the X-ray detector 320 is set to a position 19. In the second view adjacent to the first view, a position where the X-ray (second X-ray trajectory 12) which passes through the point 18 the same as the above-described point 17 (the point 17 is moved relative to the point 18 due to rotation) is incident on the X-ray detector 320 is set to a position 20. A gap width at the position 19 and the position 20 represents the gap width 15 in FIG. 4, since the X-ray focal position 10-2 of the second view is moved relative to the X-ray focal position 10-1 of the first view. On the other hand, as illustrated in FIG. 3, in the first view, a position where the X-ray (first X-ray trajectory 11) which passes through the rotation center O is incident on the X-ray detector 320 is set to a position 31. In the second view, a position where the X-ray (second X-ray trajectory 12) which passes through the rotation center O is incident on the X-ray detector 320 is set to a position 32. Accordingly, a gap width at the position 31 and the position 32 represents the gap width 13. The focus control unit 350 sets the X-ray focal position 10-2 of the second view to a position moved to the X-ray focal position 10-1 of the first view so that the gap width 15 is closer to approximately (N−½) times (N=any one of 1, 2, 3 . . . ) the channel width 24, compared to the gap width 13. In particular, it is desirable that the focus control unit 350 sets the X-ray focal position 10-2 of the second view so that the gap width 15 becomes approximately (N−½) times (N=any one of 1, 2, 3 . . . ) the channel width 24.

In this way, the focus control unit 350 sets the X-ray focal point. Accordingly, in the first region 14 distant from the rotation center O, the first X-ray trajectories 11 of the first view and the second X-ray trajectories 12 of the second view which are adjacent to each other have an interlaced relationship as illustrated in FIG. 2 (relationship in which the other X-ray trajectory 12 passes through substantially the center of the gap of one X-ray trajectory 11). In other words, in the first view and the second view, the X-ray passing through the same points 17 and 18 of the subject is incident on a position shifted as far as approximately (N−½) times (N=any one of 1, 2, 3 . . . ) the channel width 24 of the X-ray detector 320. Accordingly, it is possible to obtain the same operation effect as that when the number of channels is virtually increased. It is possible to satisfy a condition for improving resolution in the first region 14 of the subject distant from the rotation center O. In addition, sampling can be sufficiently performed on a pitch of the channel 321 of the X-ray detector 320, and it is possible to restrain an artifact in under-sampling.

In addition, it is desirable to set the X-ray focal point 10-1 of the first view and the X-ray focal point 10-2 of the second view so that positions at the coordinate system fixed to the X-ray detector of the above-described rotary plate do not overlap each other. The reason is that the number of views is substantially reduced if both of these are set to overlap each other.

The focus control unit 350 can set the position of the X-ray focal point of each view so that all of the views satisfy a relationship of the gap width of the X-ray trajectories 11 and 12 of the above-described first and second views with respect to the adjacent view. Accordingly, all of the views satisfy a condition for improving resolution in a region distant from the rotation center O. Therefore, the resolution in the region distant from the rotation center O can be improved at all rotation angles. In addition, sampling can be sufficiently performed on a pitch of the detector, and it is possible to restrain an artifact in under-sampling.

For example, the focus control unit 350 can alternately set the predetermined first X-ray focal position 10-1 and second X-ray focal position 10-2 in the order of view numbers for the multiple views. In this manner, a relationship between each view and the adjacent view can satisfy a relationship between the first view and the second view (relationship in which the gap width of the X-ray trajectory becomes approximately (N−½) times (N=any one of 1, 2, 3 . . . ) the width 24 of the channel).

Hereinafter, the X-ray CT device according to the first embodiment will be further described in detail.

<<Schematic Configuration of X-Ray CT Device>>

An overall configuration of an X-ray CT device 100 according to the embodiment of the present invention will be described with reference to FIG. 1. The X-ray CT device 100 includes an input unit 200, an imaging unit 300, a focus control unit 350, and an image generation unit 400.

<Input Unit>

The input unit 200 includes an imaging condition input unit 210. The imaging condition input unit 210 can be configured to include a keyboard 211, a mouse 212, and a monitor 213. As the monitor 213, those which have a touch panel function can be used. The monitor 213 can be used as an input device.

<Imaging Unit>

The imaging unit 300 includes an X-ray generation unit 310 provided with an X-ray tube 311, an X-ray detector 320, a gantry 330, an imaging control unit 340, and a subject mounting table 501.

The X-ray tube 311 has a flying focal spot (FFS) capability, and can change a position of an X-ray focal point 313. The X-ray detector 320 includes multiple arranged channels 321. In addition, a circular opening portion 331 for arranging the subject 500 and the subject mounting table 501 is disposed at the center of the gantry (groove support) 330. The diameter of the opening portion 331 is 700 mm as an example. The rotary plate 332 for mounting the X-ray tube 311 and the X-ray detector 320, and a drive mechanism (not illustrated) for rotating the rotary plate 332 is arranged inside the gantry 330. In addition, the subject mounting table 501 includes a drive mechanism (not illustrated) for adjusting a position of the subject 500 with respect to the gantry 330.

The X-ray detector 320 is configured to include a scintillator configuring the channel 321 or a semiconductor detector, and detects an X-ray. The X-ray detector 320 adopts a configuration in which numerous scintillators are equidistantly arrayed in an arc shape, for example, based on an average position or a gravity center position of multiple X-ray generation point positions of the X-ray tube 311. In addition, for example, the number of the channels 321 is 888. A pitch (channel pitch) in the channel direction of the respective detection elements is 1.02991 mm. In order to facilitate the production, multiple planar detectors (detector modules) can be prepared and arranged so that a central portion of the plane has an arc shape. In this manner, it is possible to use a configuration in which the planar detectors are analogously arrayed in an arc shape.

A time required for rotation of the rotary plate 332 depends on a parameter input by a user using the imaging condition input unit 210. In the present embodiment, the time required for the rotation is set to 1.0 s/time.

The number of imaging times (number of views: NumView) in one rotation of the rotary plate 332, which is called the number of views, is set to 1,058 times, for example. In this case, each time the rotary plate 332 is rotated by 0.34 degrees, the imaging is performed once. The above-described respective specifications are not limited to these values, and can be changed in various ways in accordance with the configuration of the X-ray CT device. In the configuration illustrated in FIG. 1, the rotary plate 332 is rotated clockwise as the views move forward.

The imaging control unit 340 includes an X-ray controller 341 which controls a focal position of the X-ray tube 311, a gantry controller 342 which controls rotary driving of the rotary plate 332, a table controller 343 which controls driving of the subject mounting table 501, a detector controller 344 which controls imaging of the X-ray detector 320, and an integrated controller 345. The integrated controller 345 controls each operation flow of the X-ray controller 341, the gantry controller 342, the table controller 343, and the detector controller 344.

<Image Generation Unit>

The image generation unit 400 includes a signal acquisition unit 410, a data processing unit 420, and an image display unit 440.

The signal acquisition unit 410 includes a data acquisition system (hereinafter, referred to as a DAS) 411. The DAS 411 converts a detection result of the X-ray detector 320 into a digital signal.

The data processing unit 420 includes a central processing unit (CPU) 421, a memory 422, and a hard disk drive (HDD) device 423. The central processing unit 421 and the memory 422 develop and actuate a predetermined program, thereby performing various processes such as correction calculation and image reconstruction processing. The HDD device 423 stores data, and inputs or outputs data. The image display unit 440 is configured to include an image display monitor 441 such as a liquid crystal display and a cathode ray tube (CRT).

<Focus Control Unit>

The focus control unit 350 is connected to the imaging control unit 340, and delivers a control signal to the X-ray controller 341, thereby setting a focal position for each predetermined view. An operation of the focus control unit 350 will be described in detail later.

The input unit 200 and the image generation unit 400 do not necessarily need to be integrated with the X-ray CT device 100. For example, an operation thereof may be realized by using another device connected thereto via a network. In addition, it is also possible to use a device having both functions of the image generation unit 400 and the input unit 200.

<<Imaging Method>>

Figure 5:
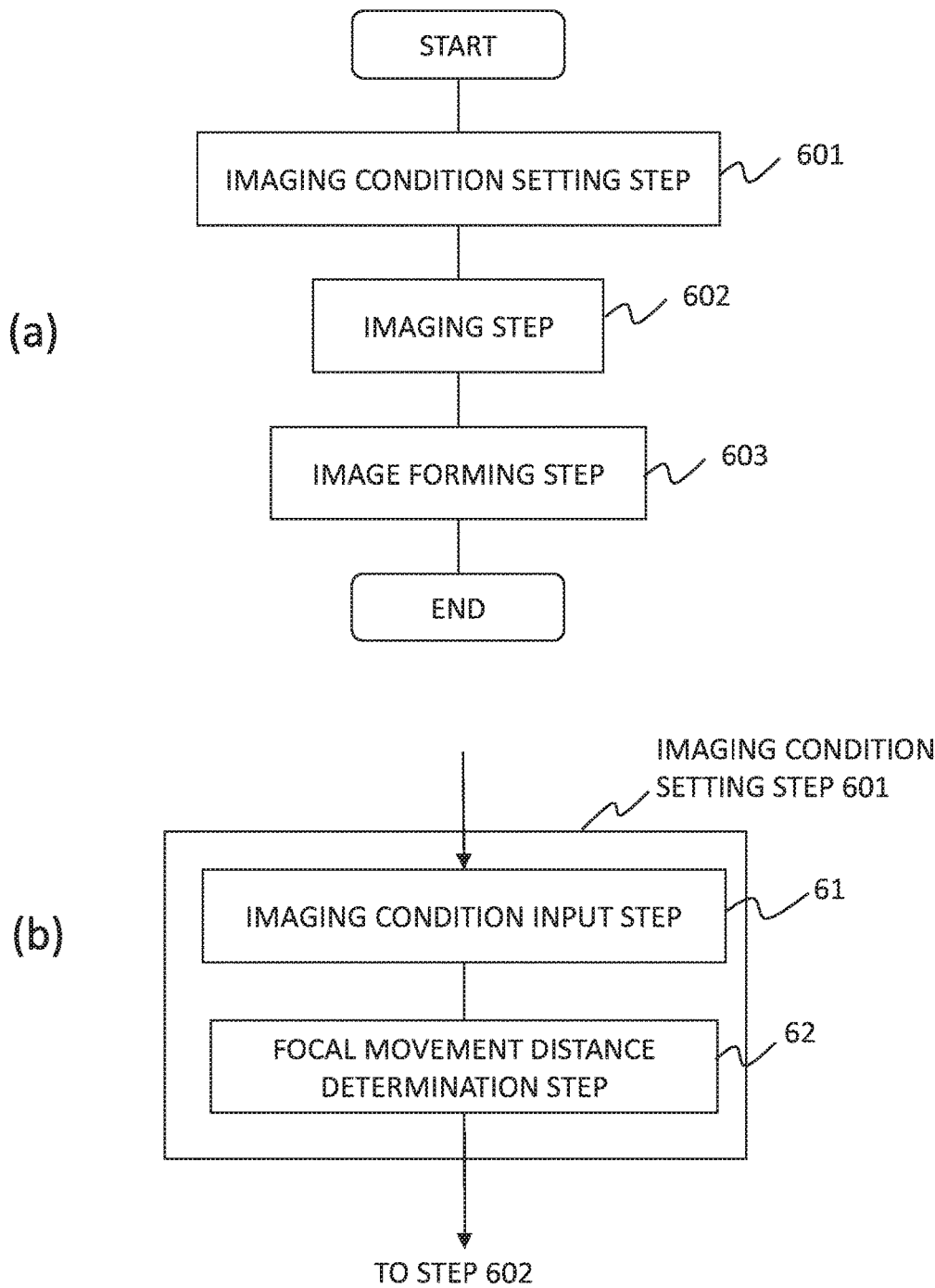
FIG. 5(a) is a flowchart illustrating an overall imaging operation of the X-ray CT device according to the first embodiment.
FIG. 5(b) is a flowchart illustrating an imaging condition setting step 601.

Hereinafter, an operation of each unit in a case where the subject is imaged by the X-ray CT device 100 will be described. The imaging is performed in the order of an imaging condition setting step 601, an imaging step 602, and an image forming step 603 as illustrated in FIG. 5.

<Imaging Condition Setting Step 601>

The imaging condition setting step 601 includes an imaging condition input step 61 and a focal movement distance determination step 62 as illustrated in FIG. 5(b). Specifically, in the imaging condition input step 61, the imaging condition input unit 210 causes the monitor 213 or another monitor to display an input screen for receiving an input from an operator. While viewing the input screen, the operator operates the mouse 212, the keyboard 211, or the touch panel sensor included in the monitor 213. In this manner, the operator sets a tube current, a tube voltage, an imaging range of the subject 500, and resolution in the X-ray tube 311. Imaging conditions can be stored in advance in a storage unit (not illustrated) inside the imaging condition input unit 200. In this case, the operator reads and uses the imaging conditions. In this manner, the operator may not input the imaging conditions whenever the imaging is performed.

Next, in the focal movement distance determination step 62, the focus control unit 350 determines a focal movement distance. A method of determining the focal movement distance will be described in detail later.

<Imaging Step>

In the imaging step 602, if the operator instructs to start the imaging via the imaging condition input unit 210, the imaging is performed under conditions such as the imaging range, the tube voltage, and the tube current amount which are set in the imaging condition setting step 601.

Specifically, the operator first disposes the subject 500 on the subject mounting table 501. The integrated controller 345 causes the table controller 343 to move the subject mounting table 501 in a direction perpendicular to the rotary plate 332. The integrated controller 345 instructs to stop the subject mounting table 501 when an imaging position of the rotary plate 332 coincides with a position designated by the operator to image the subject 500. In this manner, the subject 500 is completely disposed at the position where the subject 500 is to be imaged. The integrated controller 345 instructs the gantry controller 342 to operate a drive motor at the same timing as when the integrated controller 345 instructs the table controller 343. In this manner, the rotary plate 332 starts to be rotated.

If the rotation of the rotary plate 332 is in a constant speed state and the subject 500 is completely disposed, the integrated controller 345 instructs the X-ray controller 341 X-ray irradiation timing of the X-ray tube 311 and a position of the X-ray focal point 313 for each view in the FFS imaging.

As the X-ray focal point 313, the first embodiment provides two focal positions 10-1 and 10-2 in the direction (direction x) parallel to the longitudinal direction of the X-ray detector 320 in the coordinate system fixed to the X-ray detector 320 of the rotary plate 332 as illustrated in FIG. 2. Focal points are alternately arranged at the positions for each view.

Then, the integrated controller 345 instructs the detector controller 344 imaging timing (timing to acquire a detection signal for each view) of the X-ray detector 320. In this manner, the imaging is performed on one slice.

These instructions are repeated, thereby performing the imaging on multiple slices. A signal converted into an electrical signal after the X-ray detector 320 receives an X-ray is delivered to the DAS 411. In the DAS 411, the signal is integrated during a fixed time, and is converted into X-ray incident amount information per unit time. Thereafter, the information is stored in the HDD device 423.

In addition to the method in which the subject mounting table 501 is repeatedly moved and stopped so as to sequentially perform the imaging on the multiple slices as described above, the imaging may be performed while the subject mounting table 501 is moved as in known Helical Scan.

<Image Forming Step>

Figure 6:
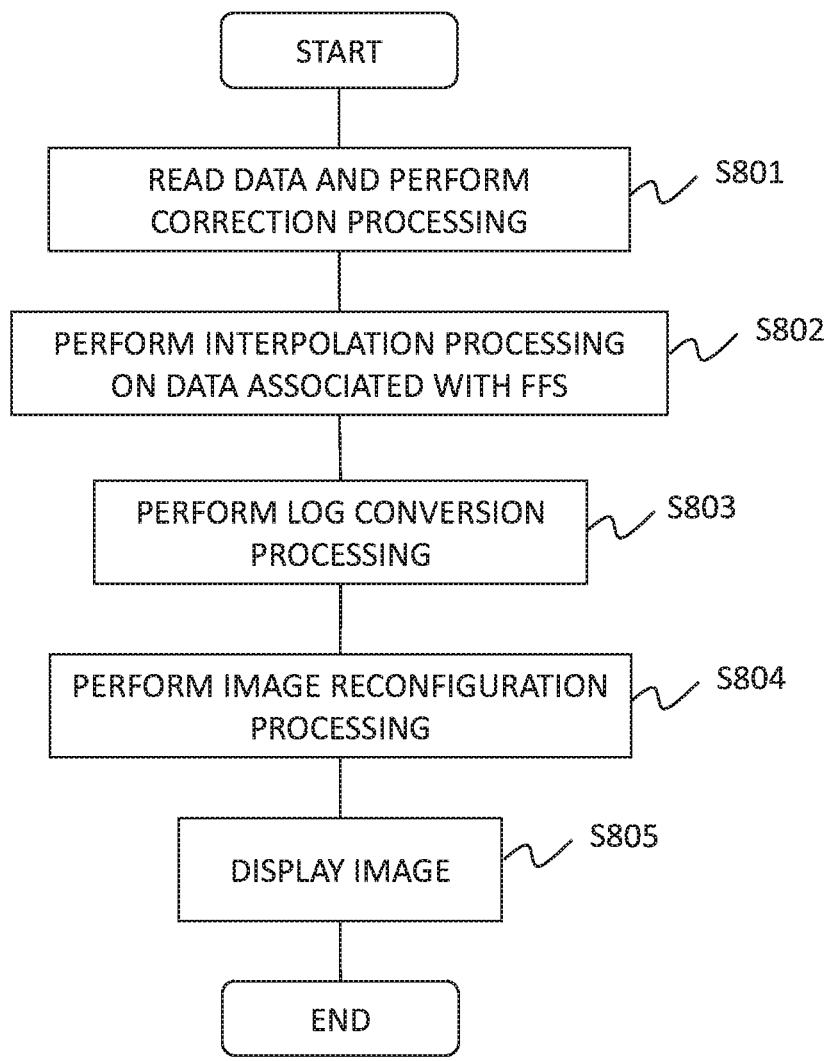
FIG. 6 is a flowchart illustrating a detailed operation of an imaging step 603 according to the first embodiment.

Next, Step 603 will be described in which data stored in the HDD device 423 is used for image forming. The calculation in Step 603 for the image forming is performed using the central processing unit 421, the memory 422, and the HDD device 423 inside the data processing unit 420 illustrated in FIG. 1. The central processing unit 421 reads and executes an image forming program stored in the memory 422 in advance, thereby generating an image as in a flow in FIG. 6.

The central processing unit 421 first reads X-ray incident amount data per unit time of the X-ray detector 320 from the HDD device 423, and performs various corrections (Step S801). For example, as correction content, a circuit linearity correction is performed using a known technique.

Next, based on the focal positions 10-1 and 10-2 for each view, interpolation processing is performed on the data associated with FFS (Step S802). This interpolation processing itself is performed similarly to interpolation processing in a known FFS technique.

Next, Log conversion or correction is performed on the interpolated X-ray incident amount data (Step S803). The Log conversion or correction is also performed using a known technique. In addition, the Log conversion can also be performed in Step S801 prior to Step S802.

Next, an image is reconstructed using the data converted by the Log conversion (Step S804). For example, the image may be reconstructed using a FeldKamp method which is a known technique, or may be reconstructed using a successive approximation or an enlarged reconstruction method which is a known technique.

Finally, the image is displayed on the image display monitor 441 (Step S805).

<Focal Movement Distance Determination Step>

Hereinafter, a method will be described in which the focus control unit 350 calculates a position (focal movement distance ΔS) of the focal positions 10-1 and 10-2 in the focal movement distance determination step 62 in FIG. 5(b).

According to the first embodiment, the focal position 10-1 and the focal position 10-2 are alternately moved for each view. In this manner, as illustrated in FIG. 4, the focal positions 10-1 and 10-2 are set so that the gap width 15 at the position (projection position) where the X-ray trajectory of each view which passes through the point 17 (18) within the first region 14 of the subject 500 at a distance R from the rotation center O reaches above the X-ray detector 320 from the focal positions 10-1 and 10-2 of each view becomes approximately (N−½) times the channel width 24. That is, the X-ray trajectories of the adjacent views are completely interlaced in the first region 14.

Figure 7:
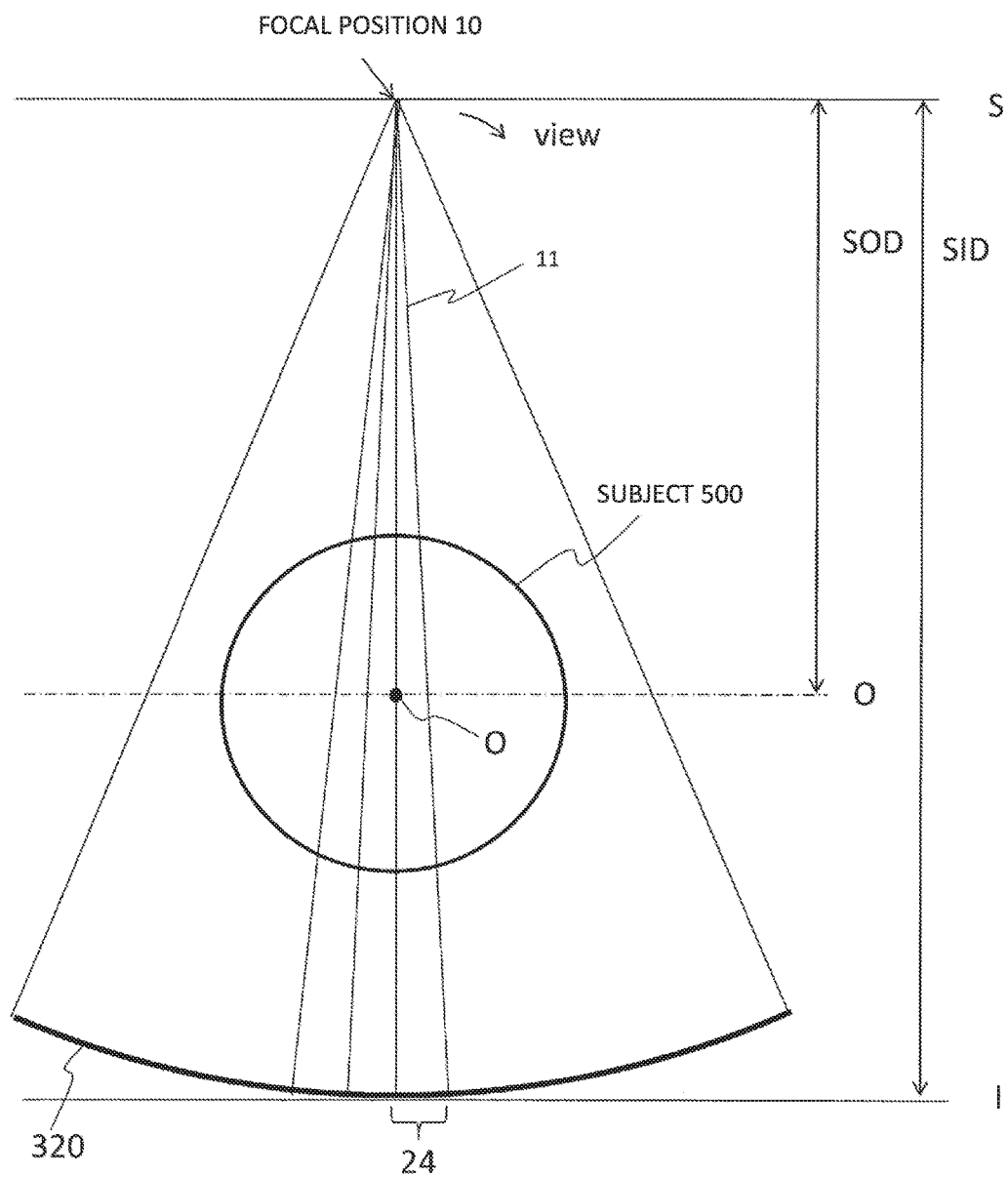
FIG. 7 is a view for describing a distance between a focal position 10, the rotation center O, and the X-ray detector 320.

Here, the first region 14 is located close to the focal positions 10-1 and 10-2 at the distance of R from the rotation center O. The above-described distance R is set to 86.7112 mm. In addition, as illustrated in FIG. 7, a distance (SID) between an X-ray generation point (focal position 10) of the X-ray tube 311 and an X-ray input surface of the X-ray detector 320 is 1,040.53 mm. A distance (SOD) between the focal position 10 and the rotation center O of the rotary plate 332 is 606.978 mm. The number of views is 1,058. The channel width 24 is 1.02991 mm.

Figure 8:
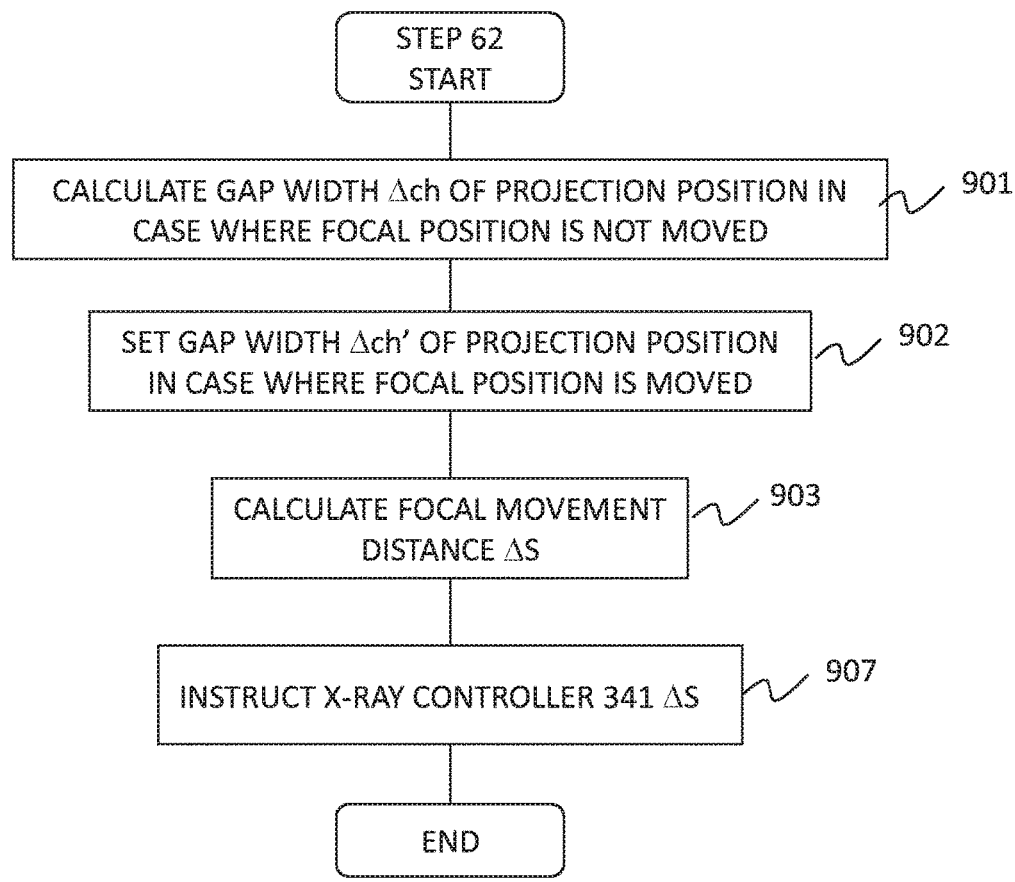
FIG. 8 is a flowchart illustrating a detailed operation in a focal movement distance determination step 62 according to the first embodiment.

The focus control unit 350 causes the incorporated CPU to read and execute a program stored in the incorporated memory, thereby calculating the focal movement distance as illustrated by a flow in FIG. 8.

First, in Step 901 in FIG. 8, the focus control unit 350 uses Expression (1) so as to calculate the gap width 15 (Δch1) between the projection position 19 of the point 17 of the subject 500 in the first view of the first region 14 and the projection position 20 of the point 18 (the same point as the point 17, after being moved by the rotation of the rotary plate 332) in the second view, in a case where the focal position 10 is not moved (in a case where 10-1 and 10-2 are the same position).

$$\Delta ch1 = R*\sin(2\pi/\text{NumView})/(SOD - R*\cos(2\pi/\text{NumView}))*SID/\text{Channel Pitch} \qquad (1)$$

Where, in Expression (1), R is the distance R of the point 17 (18) from the rotation center O, NumView is the number of views per one rotation, SOD is a distance between the focal position 10 and the rotation center O of the rotary plate 332, SID is a distance from the X-ray input surface of the X-ray detector 320, and Channel Pitch is the channel width 24. These abbreviations are similarly applied to Expression (2) below and the subsequent equations.

R=86.7112 mm, NumView=1,058, SOD=606.978 mm, SID=1,040.53 mm, and Channel Pitch=1.02991 mm are substituted into Expression (1) so as to calculate Δch1 (gap width 15). A value of Δch1 (gap width 15) is obtained as a value substantially equal to that of the channel width 24. That is, the value shifted by 1ch (channel) is obtained. If the viewing direction is set to the clockwise direction in the movement direction, the movement direction of the projection position 19 is the leftward direction. If the leftward direction is expressed by minus (−), in a case where the focal position 10-1 is not moved, the movement between views is expressed by −1ch (channel).

Next, in Step 902, in a case where the focal position for each view is moved from the focal position 10-1 to the focal position 10-2, the focus control unit 350 sets a desired value (predetermined value) as the gap width 15 (Δch1') generated at the projection positions 19 and 20 between views of the point 17 (18) within the first region 14. Here, in order to realize the interlaced relationship, for example, Δch1'=−1.5ch is set so as to be shifted leftward as far as approximately (N−½) times (where N=any one of 1, 2, 3 . . . ) the channel width 24. Here, as the value of Δch1', the predetermined value is used. However, the value may be determined, based on an operator's input to the imaging condition input unit 210.

In this manner, the projection trajectory 11 of the first view and the projection trajectory 12 of the second view are interlaced by being located at exactly the center of the interval one another in the first region 14. This state is referred to as a completely interlaced state.

Next, in Step 903 in FIG. 8, the focus control unit 350 calculates a focal movement distance ΔS1 from the focal position 10-1 to the focal position 10-2 in order to realize the desired gap width 15 (Δch1') set in Step 902 with regard to the point within the first region 14. ΔS1 can be calculated using.

Expression (2).

$$\Delta S1=(\Delta ch1-\Delta ch1')*\text{Channel Pitch}*(SOD-R)/(SID-SOD+R) \quad (2)$$

In Step 907 in FIG. 8, the focus control unit 350 instructs the integrated controller 345 the focal movement distance ΔS1 set in Step 903 as ΔS.

In this manner, in the imaging step 602 in FIG. 5(a), the integrated controller 345 controls the X-ray controller 341 so as to set the focal position 10-2 at a distance of ΔS from the focal position 10-1. Then, the imaging is performed by alternately setting the focal positions 10-1 and 10-2 for each view.

Figure 9:
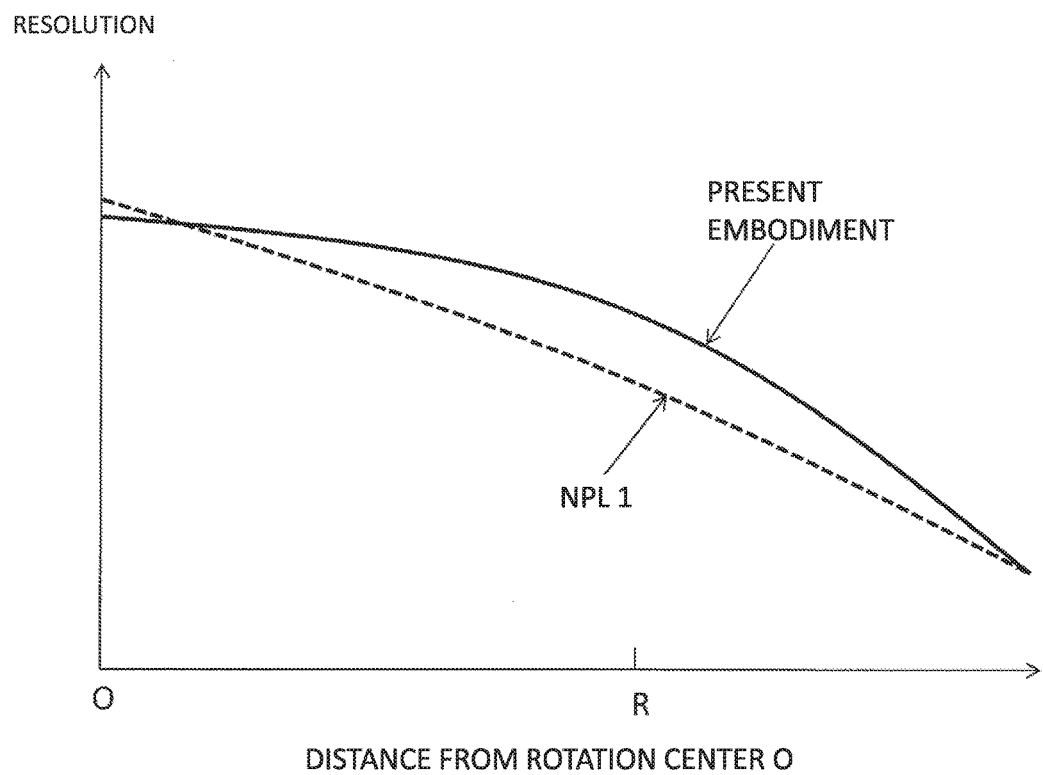
FIG. 9 is a graph illustrating a relationship between resolution of an image obtained by the X-ray CT device according to the first embodiment and a distance from the rotation center inside the image.

As described above, according to the first embodiment, the focus control unit 350 calculates the focal movement distance ΔS, and alternately setting the focal position 10-1 and the focal position 10-2. Accordingly, compared to an image obtained using the FFS method disclosed in NPL 1, the X-ray CT image can have improved spatial resolution (resolution) in a annulus-shaped peripheral region that is the vicinity of the distance R from the rotation center O as typically illustrated in FIG. 9.

In the above-described first embodiment, a case has been described where the first region 14 is located close to the focal positions 10-1 and 10-2 from the rotation center O. However, without being limited to the position, the first region 14 can be set to any desired position.

According to the first embodiment, the focus control unit 350 is configured to instruct the integrated controller 345 by performing a flow in FIG. 8 and calculating the focal movement distance ΔS whenever the imaging is performed. However, a configuration may be adopted in which the calculation in the flow in FIG. 8 is performed in advance so as to calculate the focal movement distance ΔS and the focal movement distance ΔS is stored in the incorporated memory. Then, in Step 62 in FIG. 5 (b), after reading the focal movement distance ΔS stored in the memory of the focus control unit 350, the focus control unit 350 instructs the integrated controller 345.

Second Embodiment

A second embodiment according to the present invention will be described. In Step 902 in FIG. 8 according to the first embodiment, an example has been described in which the focal movement distance ΔS is set so that the gap width 15 generated at the projection positions 19 and 20 between all of the views is shifted leftward as far as exactly (N−½) times (where N=any one of 1, 2, 3 . . . ) the channel width 24. In the present invention, the gap width 15 may not necessarily satisfy the condition of exactly (N−½) times.

In the second embodiment, an example will be described with reference to FIG. 10 in which the focal movement distance ΔS is set so that the gap width 15 generated at the projection positions 19 and 20 between approximately an half of views within some continuous views satisfies approximately (N−½) times (where N=any one of 1, 2, 3 . . . ) the channel width 24, and so that the gap width 15 generated at the projection positions 19 and 20 between the remaining views satisfies approximately N times (where N=any one of 0, 1, 2, 3 . . . ) the channel width 24, that is, so that the interlaced relationship is satisfied as a whole in some views. The focal position 10-1 of the first view is a focal position of the leading view in some continuous views, and the focal position 10-2 of the second view is a focal position of the other view in some continuous views.

Figure 10:
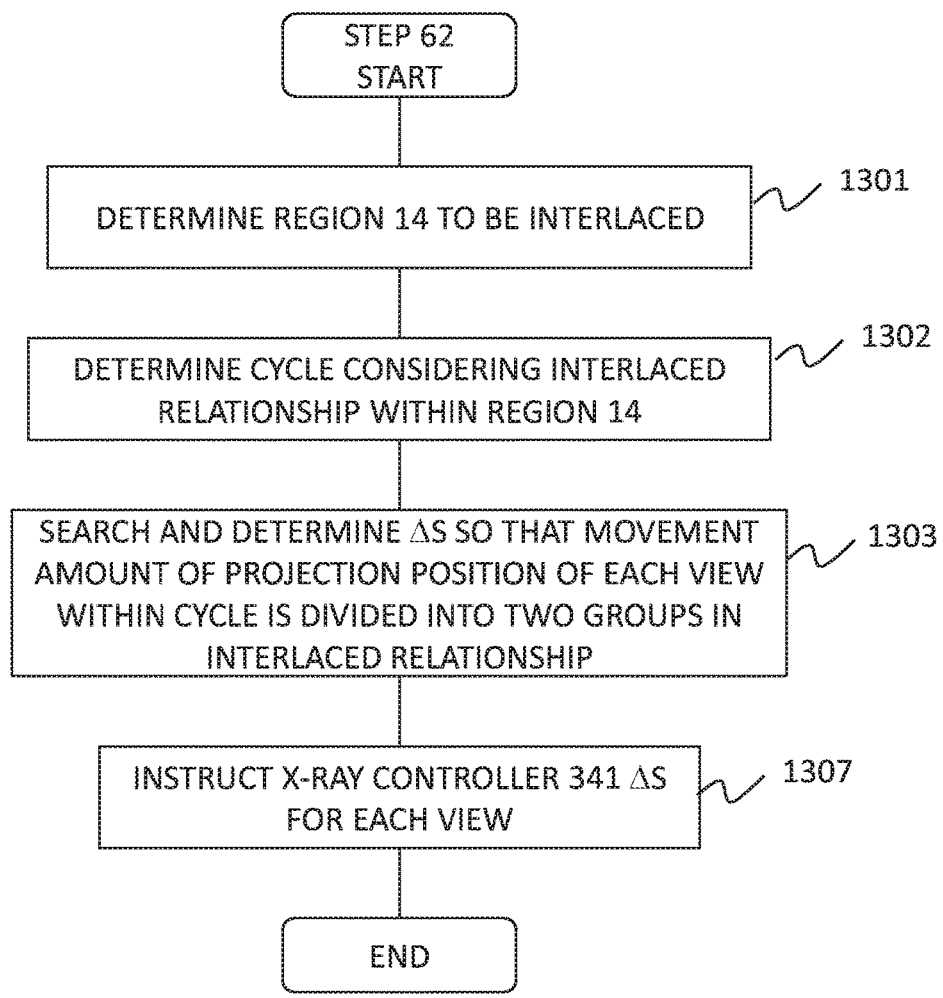
FIG. 10 is a flowchart illustrating a detailed operation in the focal movement distance determination step 62 according to a second embodiment.

The focus control unit 350 performs respective Steps 1301 to 1304 in a flow in FIG. 10 as the focal movement distance determination step 62 in FIG. 5(b).

First, in Step 1301, the focus control unit 350 determines a position of the first region 14 to be interlaced. For example, the focus control unit 350 can receive the position of the first region 14 from an operator via the imaging condition input unit 210.

Next, in Step 1302, the focus control unit 350 sets a cycle of interlaced views. The cycle of the interlaced views is the number of continuous views considering the interlaced relationship, and is set to one cycle with four views, for example. The focal movement distance is set so that the gap width 15 generated at the projection positions 19 and 20 between approximately an half of the views included in this one cycle satisfies approximately (N−½) times (where N=any one of 0, 1, 2, 3 . . . ) the channel width 24, and so that the gap width 15 generated at the positions 19 and 20 between the remaining views satisfies approximately N times (where N=any one of 1, 2, 3 . . . ) the channel width 24. For example, the focus control unit 350 can also set a forcibly predetermined number, for example, two views, as one cycle. In addition, the focus control unit 350 can calculate the gap width 15 between the views having no focal movement. If the gap width 15 is approximately one time≅1/1 or approximately 0.75 times≅3/4 the channel width 24, the focus control unit 350 can set 2 or 8 obtained by doubling a value of the denominator as the number of views in one cycle. The reason is as follows. In a case where the number of views two times the denominator is set, the focal positions 10-1 and 10-2 are set for each view in the cycle. In this manner, it is possible to relatively easily set the focal movement distance ΔS which generates substantially every half of the gap width 15 which is approximately (N−½) times and the gap width 15 which is approximately N times.

The focus control unit 350 can also receive the number of views in one cycle from an operator via the imaging condition input unit 210.

Next, in Step 1303, the focus control unit 350 searches for a focal movement amount ΔS in which the gap width 15 of approximately the half in the multiple views within one cycle becomes approximately N times (where N=any one of 0, 1, 2, 3 . . . ) the channel width 24 and so that the gap width 15 of the other remaining half becomes approximately (N-½) times (where N=any one of 1, 2, 3 . . . ) the channel width 24. For example, in a case of one cycle with four views, the focus control unit 350 searches for the focal movement amount ΔS as follows so that the gap width 15 in the four views becomes approximately N times twice and so that the gap width 15 becomes approximately (N-½) times twice in the remaining views.

The gap width 15 (Δch1') after focal movement can be expressed as in Expression (3) by using the focal movement distance ΔS, based on Expression (2) according to the first embodiment.

$$\Delta ch1' = \Delta ch1 - \Delta S/\text{Channel Pitch}/(SOD-R)*(SID-SOD+R) \quad (3)$$

Then, the focus control unit 350 searches for ΔS in which the evaluation function of Expression (4) below is minimized.

[Expression 4]

$$\sum_{lower} |\text{Fraction}(\Delta ch1') - 0.5| + \sum_{lower} |\text{Fraction}(\Delta ch1' + 0.5) - 0.5| \quad (4)$$

In Expression (4), $$\sum_{lower} x$$

represents that the half is selected and added from those which have a smaller value in all values x corresponding to the above-described one cycle. Fraction (x) represents a fractional part.

Accordingly, the first term in Expression (4) means a group of views whose projection position is shifted from the projection position of the leading view as far as 0.5ch or a value obtained by adding an integer to 0.5ch. Specifically, for example, in a case where the number of all views included in one cycle is four, the first term shows a result that two values are selected and added from the smaller values within values obtained by subtracting 0.5 from the fractional part of the gap width 15 (Δch1') between the four views. That is, the first term represents a total shifted amount from (N-½) times (where N=any one of 1, 2, 3 . . . ) Δch1' between the views in which Δch1' becomes approximately (N-½) times the channel width 24.

The second term in Expression (4) means a group of views whose projection position is not shifted or is shifted at integer multiples from the projection position of the leading view. Specifically, for example, in a case where the number of all views included in one cycle is four, the second term shows a result that two values are selected and added from the smaller values within values obtained by subtracting 0.5 from the fractional part obtained by adding 0.5 to the gap width 15 (Δch1') between the four views. That is, the second term represents a total shifted amount from N times (where N=any one of 0, 1, 2, 3 . . . ) Δch1' between the views in which Δch1' becomes approximately N times the channel width 24.

Therefore, it is possible to obtain the focal movement amount ΔS in which the gap width 15 in the half of the multiple views within one cycle becomes approximately N times (where N=any one of 0, 1, 2, 3 . . . ) the channel width 24 and the gap width 15 in the other remaining half becomes approximately (N-½) times (where N=any one of 1, 2, 3 . . . ) the channel width 24 by the focus control unit 350 searching for ΔS in which Expression (4) as a total sum of the first term and the second term is minimized.

In Step 1304, the focus control unit 350 instructs the X-ray controller 341 the focal movement distance ΔS1 for each view.

Step 62 is performed as described above so as to set the focal movement distance ΔS. Accordingly, in the continuous views, a view which achieves the interlaced relationship and a view which does not achieve the interlaced relationship are alternately generated. In this manner, it is possible to improve resolution in a region at a distance of R from the rotation center O.

Third Embodiment

Figure 11:
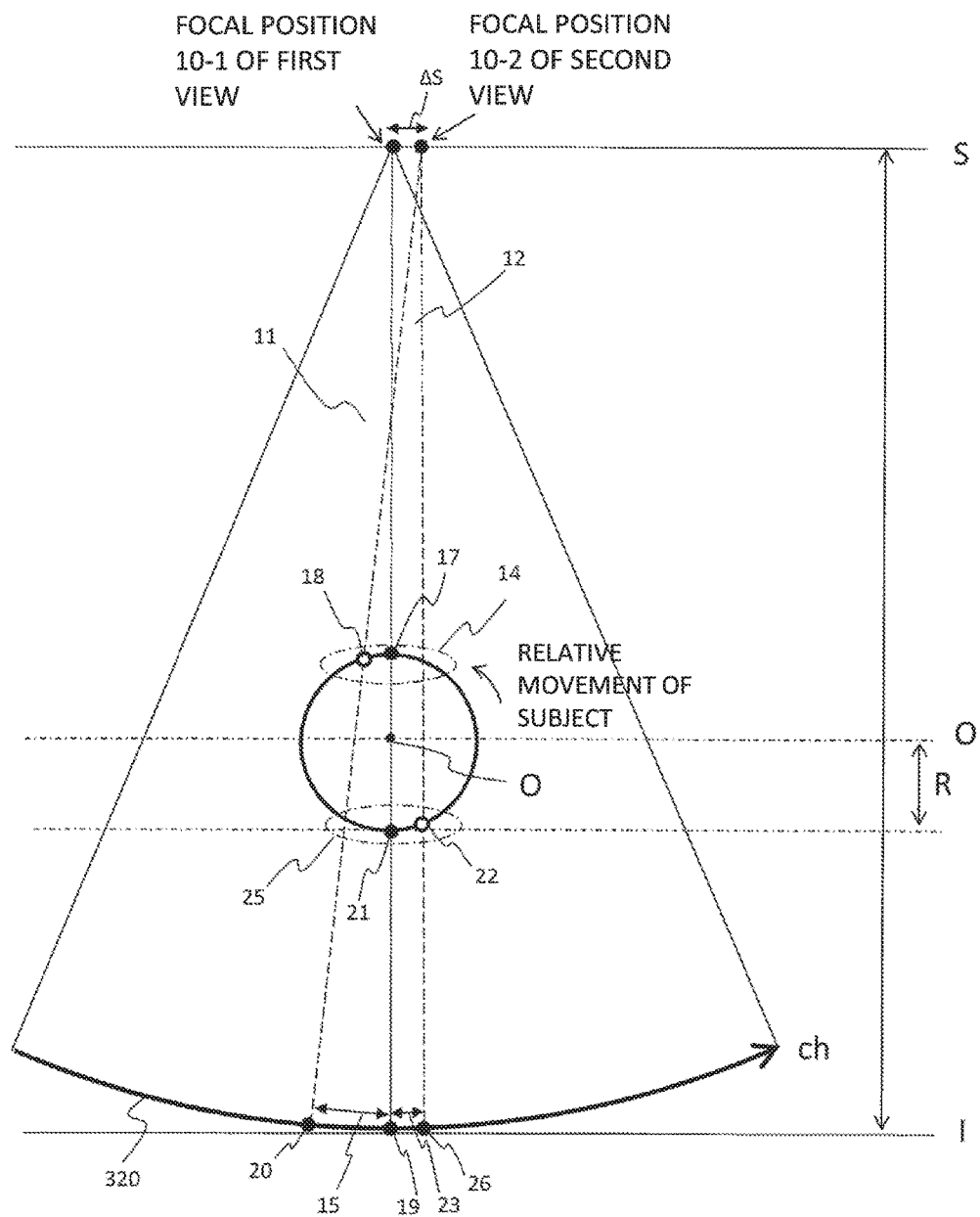
FIG. 11 is a view for describing a gap width 23 in the X-ray detector 320 of the X-ray trajectories 11 and 12 which pass through the same point 21 (22) within a second region 25, in the coordinate system fixed to the X-ray detector of the rotary plate.

A third embodiment will be described. According to the third embodiment, as in the first embodiment, the interlaced relationship is achieved within the first region 14 close to the focal positions 10-1 and 10-2 from the rotation center O. At the same time, as illustrated in FIG. 11, the interlaced relationship is also achieved at the same point 21 (22) of the subject 500 within a predetermined second region 25 close to the X-ray detector 320 from the rotation center O of the subject 500. That is, the X-ray focal position 10-2 of the second view is set so that a gap width 23 between the first X-ray trajectory 11 and the second X-ray trajectory 12 which pass through the same point 21 (22) in the second region 25 becomes approximately (N-½) times (N=any one of 1, 2, 3 . . . ) the channel width 24, compared to the gap width 13 (refer to FIG. 3) of the projection positions on the X-ray detector 320 of the first X-ray trajectory 11 and the second X-ray trajectory 12 which pass through the rotation center O. Here, the point 21 is a point of the subject 500 within the second region 25 in the first view. The point 22 is a point of the subject 500 in the second view, and the point 22 is the same point as the point 21. The subject 500 is rotated and moved relative to the rotary plate 332, thereby moving the point 21 to the point 22.

Specifically, the focal positions 10-1 and 10-2 are set so that the gap width 23 at a position (projection position) where the X-ray trajectory of each view which passes through the point 21 (22) within the second region 25 of the subject 500 located close to the X-ray detector 320 at the distance of R from the rotation center O reaches above the X-ray detector 320 from the focal positions 10-1 and 10-2 of each view becomes approximately (N-½) times the channel width 24.

In this manner, a substantially interlaced operation effect can be obtained not only in the first region 14 shifted toward the X-ray detector 320 side from the rotation center O but also in the second region 25. It is possible to obtain an advantageous effect which is the same as that when the number of channels is virtually increased. Accordingly, it is possible to satisfy a condition for improving resolution in the second region 25 of the subject distant from the rotation center O. In addition, it is also possible to restrain an artifact in under-sampling.

The focal positions 10-1 and 10-2 can be set so that the above-described first region 14 and second region 25 are located on a line reaching the X-ray detector 320 from the X-ray tube 311 through the rotation center O.

A specific operation of the focus control unit 350 will be described with reference to FIG. 12. In a flow in FIG. 12, the same process as that in the flow in FIG. 8 will be briefly described. First, in Step 901, the gap width 15 (Δch1) is calculated for the point 17 (18) in the first region 14. In addition, in a case where the focal position 10 is not moved, the focus control unit 350 calculates the gap width 23 (Δch2) between the projection position 19 of the point 21 of the subject 500 in the first view in the second region 25 and the projection position 26 of the point 22 (the same point as the point 21, after being relatively moved by the rotation of the rotary plate 332) in the second view, based on Expression (5) which is the same as Expression (1).

$$\Delta ch2 = R*\sin(2\pi/\text{NumView})/(SOD+R*\cos(2\pi/\text{NumView}))*SID/\text{Channel Pitch} \quad (5)$$

If Δch2 is calculated by substituting the numerical value described in the first embodiment into Expression (5), a value of Δch2 (gap width 23) is obtained as a value of approximately 0.75 times the channel width 24. In addition, the movement direction is the rightward direction. Accordingly, it is understood that every +0.75ch is moved between views in a case where the focal position 10-1 is not moved.

Next, similarly to the first embodiment, in Step 902, the focus control unit 350 sets desired Δch1' for the point 17 (18) in the first region 14 in a case where the focal position is moved. In addition, the focus control unit 350 sets a desired value (predetermined value) as the gap width 23 (Δch2') which is generated at the projection positions 21 and 22 between views of the point 21 (22) within the second region 25 by the movement from the focal position 10-1 to the focal position 10-2. Here, in order to achieve the interlaced relationship in the second region 25, for example, the focus control unit 350 sets Δch2'=−0.5ch so as to be shifted rightward as far as approximately (N−½) times (where N=any one of 1, 2, 3 ...) the channel width 24. Here, as the value of Δch1', a predetermined value is used. However, the value may be determined, based on an operator's input to the imaging condition input unit 210.

Figure 12:
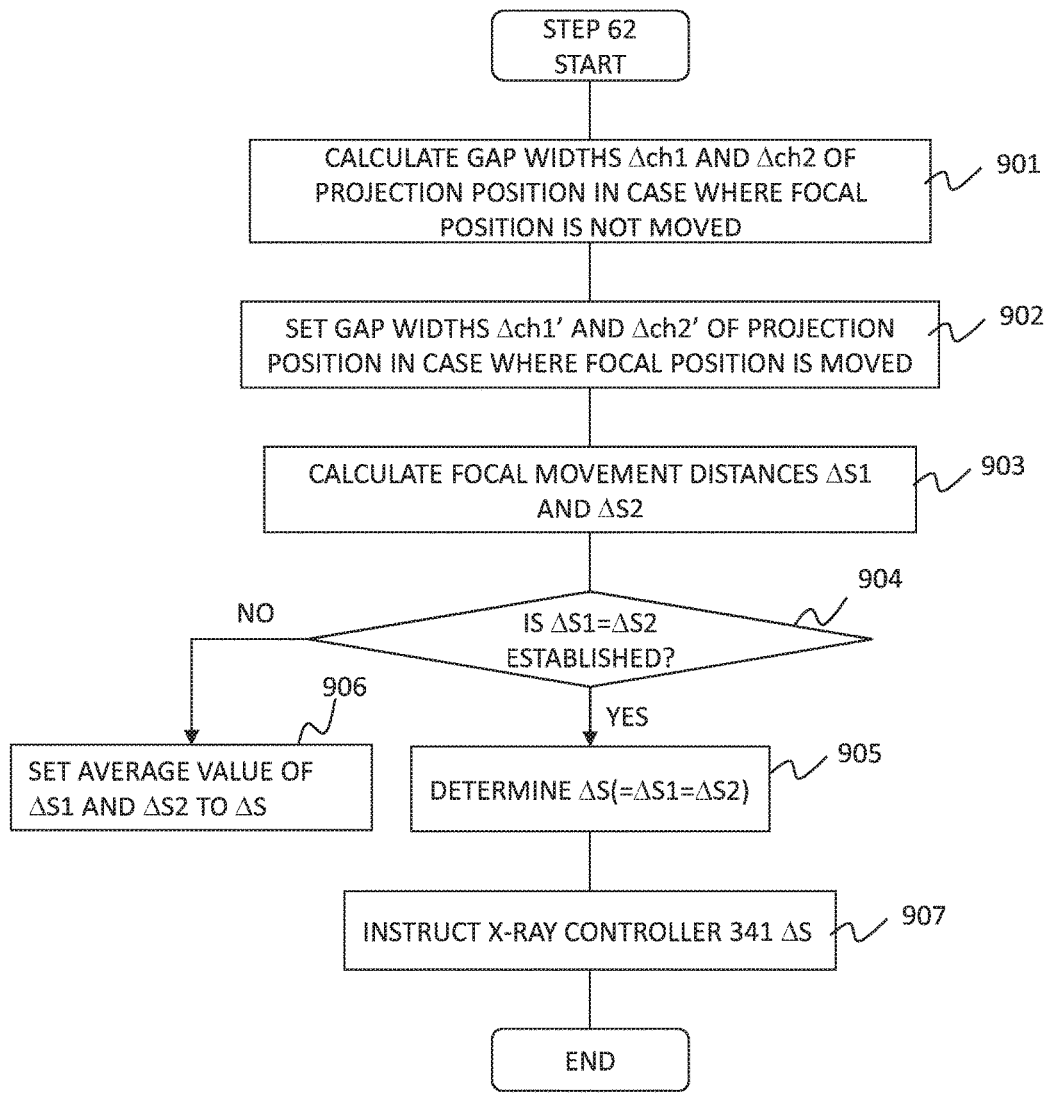
FIG. 12 is a flowchart illustrating an operation in the focal movement distance determination step 62 according to a third embodiment.

Next, in Step 903 in FIG. 12, the focus control unit 350 calculates the focal movement distance ΔS1 in order to realize the desired gap width 15 (Δch1') for the point within the first region 14. Similarly to the first embodiment, the focal movement distance ΔS1 is calculated. In addition, the focus control unit 350 calculates the focal movement distance ΔS2 from the focal position 10-1 to the focal position 10-2 in order to realize the desired gap width 23 (Δch2') set for the point within the second region 25, based on Expression (6).

$$\Delta S2 = (\Delta ch2 - \Delta ch2')*\text{Channel Pitch}*(SOD+R)/(SID-SOD-R) \quad (6)$$

In order to realize the gap width (interlaced relationship) of (N−½) times in both of the above-described first region 14 and second region 25, ΔS1=ΔS2 needs to be established. In Step 904 in FIG. 12, the focus control unit 350 determines whether or not ΔS1=ΔS2 is established. The above-described Δch1'=−1.5ch and Δch2' 0.5ch can realize ΔS1=ΔS2. In a case where ΔS1=ΔS2 is established, the process proceeds to Step 905, and sets ΔS=ΔS1=ΔS2 as the focal movement distance ΔS. In this manner, the interlaced relationship can be realized in the first region 14 and the second region 15.

On the other hand, in Step 904, in a case where ΔS1=ΔS2 is not established, the process proceeds to Step 906. An average value of ΔS1 and ΔS2 is obtained, and the average value is set as the focal movement distance ΔS. In this case, it is possible to realize a state close to the interlaced relationship in both the first region 14 and the second region 15.

In addition, in Step 906, any one of ΔS1 and ΔS2 can be selected so as to be set as the focal movement distance ΔS. In this case, the interlaced relationship can be realized in only any one of the first region 14 and the second region 15.

In addition, in step 904, in a case where ΔS1=ΔS2 is not established, the process returns to Step 902. In this manner, Δch1' and Δch2' can be set again.

Figures 13, 14:
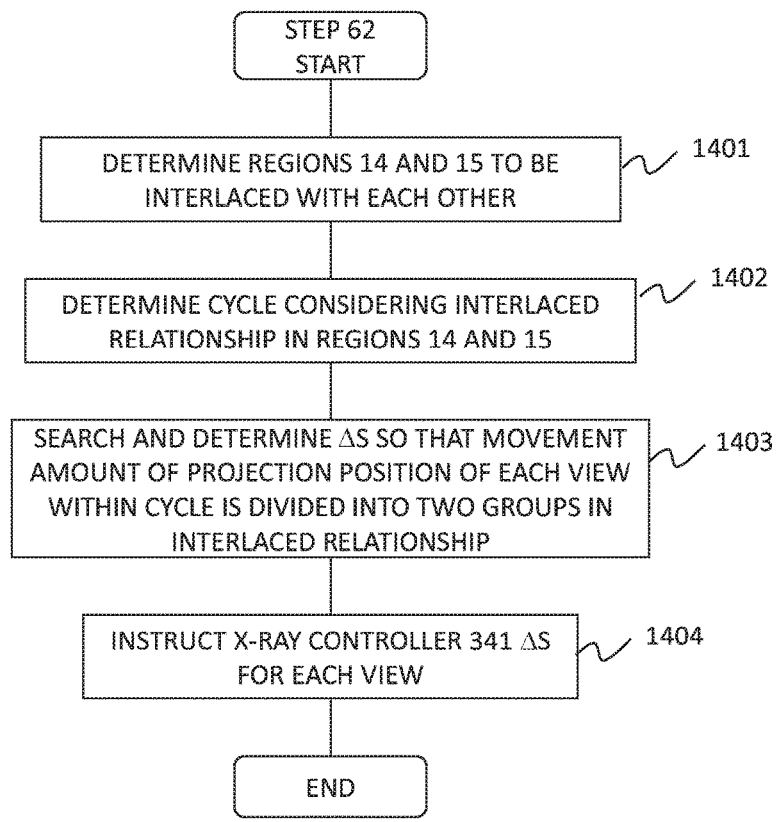
FIG. 13 is a view using a tabular format for describing focus shift of each view and a movement amount of a projection position of a point within first and second regions according to the third embodiment.
FIG. 14 is a flowchart illustrating a detailed operation in the focal movement distance determination step 62 according to a fourth embodiment.

Here, in a case where the focal position 10-1 and the focal position 10-2 for each view are alternately moved as the movement distance ΔS (=ΔS1=ΔS2) of the focal position 10-1 and the focal position 10-2, the movement amount of the projection position 19 (20, . . . ) of the point 17 (18, . . . ) within the first region 14 is illustrated in FIG. 13. The movement amount of the projection position 19 (26, . . . ) of the point 21 (22, . . . ) within the second region 25 is also illustrated in FIG. 13. In FIG. 13, the movement amount of the projection position 19 of the first view is set to zero.

As is apparent from FIG. 13, the gap width 15 (Δch1') of the projection position of the point in the first region 14 between the first view and the second view is −1.5ch. In addition, the gap width 15 (Δch1') between the second view and the third view is −2−(−1.5)=−0.5ch. The gap width 15 (Δch1') between the third view and the fourth view is −3.5−(−2)=−1.5ch. The gap width 15 (Δch1') between the fourth view and the fifth view is −4−(−3.5)=−0.5ch. All of these achieve the gap width of (N−½) times (where N=any one of 1, 2, 3 ... ). Therefore, the completely interlaced state for each view is achieved in the first region 14. It is possible to improve resolution of the image of the subject in the first region 14 distant from the rotation center O.

On the other hand, the gap width 23 (Δch2') of the projection position of the point in the second region 25 is +0.5ch between the first view and the second view, is 1.5−0.5=1.0ch between the second view and the third view, is 2−1.5=0.5ch between the third view and the fourth view, and is 3−2=1ch between the fourth view and the fifth view. Accordingly, the gap width 23 (Δch2') is (N−½) times (where N=any one of 1, 2, 3 ... ) between the first view and the second view, and between the third view and the fourth view, thereby achieving the interlaced relationship.

In the second region 25, the gap width 23 (Δch2) in a case where there is no focal movement is 0.75ch as obtained from Expression (2) above. Accordingly, in the four view cycle, the second region 25 is moved at integer multiples of the channel width 24. Therefore, it is difficult to simultaneously achieve the interlaced relationship of (N−½) times for each view in the second region 25 while achieving the interlaced relationship of (N−½) times for each view in the first region 14. However, it is possible to achieve the interlaced relationship of (N−½) times twice within the four view cycle by setting the focal movement distance ΔS as in the present embodiment. Accordingly, the interlaced operation effect can also be obtained for the image of the subject in the second region 25, and it is possible to improve resolution of the image of the subject in the second region 24 distant from the rotation center O.

Other configurations according to the third embodiment are the same as those according to the first embodiment, and thus, description thereof will be omitted.

According to the third embodiment, a configuration may be adopted in which the focus control unit 350 performs calculation in a flow in FIG. 12 in advance, calculates the focal movement distance ΔS, and stores the focal movement distance ΔS in the incorporated memory. Then, in Step 62 in FIG. 5(b), the focus control unit 350 reads the focal movement distance ΔS stored in the memory of the focus control unit 350, and instructs the integrated controller 345 the focal movement distance ΔS. In this case, gap widths (Δch1' and Δch2') in which ΔS1 and ΔS2 are equal to each other can be obtained and stored in advance. Accordingly, the interlaced relationship can be simultaneously and easily realized in the first and second regions. In addition, in Step 902 in FIG. 12, in a case where a desired value of the gap widths (Δch1' and Δch2') is received from an operator, a configuration can also be adopted in which each ΔS is obtained for combinations of multiple receivable types of Δch1' and Δch2' and an operator selects one combination from the multiple types of Δch1' and Δch2'.

Fourth Embodiment

A fourth embodiment according to the present invention will be described. In Step 903 according to the third embodiment, the focal movement distance ΔS is set so as to realize the interlaced relationship in which the gap width 15 generated at the projection positions 19 and 20 between all of the views in the first region 14 is shifted leftward as far as exactly (N−½) times (where N=any one of 1, 2, 3 . . . ) the channel width 24, and simultaneously in which the gap width 23 of the projection position between a view and the adjacent view in the four view cycle in the second region 25 becomes exactly (N−½) times (where N=any one of 1, 2, 3 . . . ). However, according to the present invention, the gap width 15 of the projection position between all of the views may not necessarily satisfy the condition of exactly (N−½) times. The focal position 10-1 of the first view is a focal position of the leading view in some continuous views, and the focal position 10-2 of the second view is a focal position of the other view in some continuous views.

In the fourth embodiment, the following example will be described with reference to FIG. 14. The focal movement distance ΔS is set so that the gap width 15 generated at projection positions 19 and 20 in approximately an half of the views in some continuous views satisfies approximately (N−½) times (where N=any one of 1, 2, 3 . . . ) the channel width 24, and so that the gap width 15 generated at projection positions 19 and 20 in the remaining views satisfies approximately N times (where N=any one of 0, 1, 2, 3 . . . ) the channel width 24.

The focus control unit 350 performs each of Steps 1401 to 1404 in a flow in FIG. 14 as the focal movement distance determination step 62 in FIG. 5(b).

First, in Step 1401, the focus control unit 350 determines a position of the first region 14 and the second region 25 which are to be interlaced with each other. For example, the position of the first region 14 and the second region 25 can be received from an operator via the imaging condition input unit 210.

In Step 1402, the focus control unit 350 sets each cycle of interlaced views for respective regions 14 and 25. This process is performed similarly to Step 1302 according to the second embodiment.

In Step 1403, the focus control unit 350 searches for the focal movement amount ΔS in which the gap width 15 of approximately the half in the multiple views within one cycle in both the first region 14 and the second region 25 becomes approximately N times (where N=any one of 0, 1, 2, 3 . . . ) the channel width 24 and so that the gap width 15 of the other remaining half becomes approximately (N−½) times (where N=any one of 1, 2, 3 . . . ) the channel width 24. For example, in a case of one cycle with four views, the focus control unit 350 searches for the focal movement amount ΔS as follows so that the gap width 15 for two views in the four views becomes approximately N times and so that the gap width 15 becomes approximately (N−½) times in the remaining two views.

The gap width 15 (Δch1') and the gap width 23 (Δch2') after focal movement can be expressed as in Expressions (7) and (8) by using the focal movement distance ΔS.

$$\Delta ch1' = \Delta ch1 - \Delta S/\text{Channel Pitch}/(SOD-R)*(SID-SOD+R) \quad (7)$$

$$\Delta ch2' = \Delta ch2 - \Delta S/\text{Channel Pitch}/(SOD+R)*(SID-SOD-R) \quad (8)$$

There, the focus control unit 350 searches for ΔS in which the evaluation function of Expression (9) below is minimized.

[Expression 9]

$$\sum_{lower} |\text{Fraction}(\Delta ch1') - 0.5| + \sum_{lower} |\text{Fraction}(\Delta ch1' + 0.5) - 0.5| + \\ \sum_{lower} |\text{Fraction}(\Delta ch2') - 0.5| + \sum_{lower} |\text{Fraction}(\Delta ch2' + 0.5) - 0.5| \quad (9)$$

In Expression (9), $$\sum_{lower}$$

represents that the half of all values is selected and added from those which have a smaller value in all values (included in a symbol ||) corresponding to the above-described one cycle. Fraction (x) represents a fractional part of x.

Therefore, the focus control unit 350 searches for ΔS in which Expression (9) is minimized. In this manner, it is possible to obtain the focal movement amount ΔS in which the gap width 15 in the half of the multiple views within one cycle becomes approximately N times (where N=any one of 0, 1, 2, 3 . . . ) the channel width 24 and the gap width 23 in the other remaining half becomes approximately (N−½) times (where N=any one of 1, 2, 3 . . . ) the channel width 24.

In Step 1404, the focus control unit 350 instructs the X-ray controller 341 the focal movement distance ΔS1 for each view.

Step 62 is performed as described above so as to set the focal movement distance ΔS. Accordingly, in the continuous views, approximately a half of views are interlaced with each other. In this manner, it is possible to improve resolution in a region at a distance of R from the rotation center O.

Other configurations according to the fourth embodiment are the same as those according to the first and second embodiments, and thus, description thereof will be omitted.

Fifth Embodiment

An X-ray CT device according to a fifth embodiment will be described with reference to FIGS. 15 and 16.

The first embodiment adopts a configuration in which the focus control unit 350 calculates the focal movement distance ΔS and in which the focal position 10-1 and the focal position 10-2 are alternately set so as to perform imaging. However, according to the fifth embodiment, the focus control unit 350 calculates the focal position movement amount ΔS for each view, and sets positions 10-1, 10-2, . . . of the X-ray focal point so that the gap width 15 (Δch1') generated at the projection position of the point in the first region 14 becomes a desired value for each view.

Figure 15:
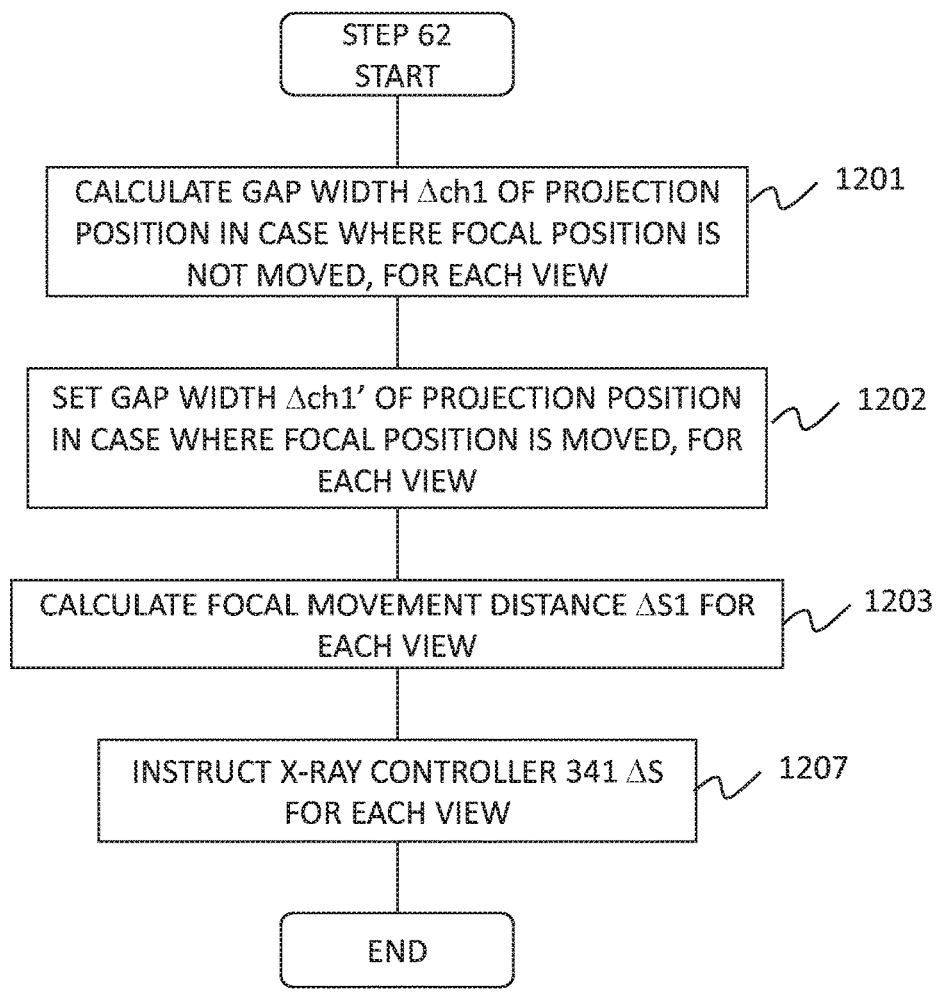
FIG. 15 is a flowchart illustrating a detailed operation in the focal movement distance determination step 62 according to a fifth embodiment.

Specifically, in Step 62 in FIG. 5(b), the focus control unit 350 calculates the focal movement distance ΔS for each view as in a flow in FIG. 15.

First, in Step 1201, the focus control unit 350 calculates the gap width 15 (Δch1) of the projection position between the respective views in a case where the focal position 10 is not moved, similarly to the first embodiment, based on Equation (1) in the first embodiment. Here, as an example, as illustrated in FIG. 16, Δch1=1.1ch is set. In FIG. 16, a projection position movement amount obtained by accumulating the gap width 15 (Δch1) for each view is also illustrated together. Here, the movement amount of the projection position 19 in the first view is illustrated as zero.

Next, in Step 1202, the focus control unit 350 sets a desired value for each view-to-view as each gap width (Δch1') of the projection position between the views in a case where the focal position is moved for each view. For example, the focus control unit 350 sets each value which satisfies (N−½) times (where N=any one of 1, 2, 3 . . . ) so that the gap width is 1.5ch between the first view and the second view and the gap is 0.5ch between the second view and the third view, thereby realizing the interlaced relationship. Here, as a value of Δch1' for each view-to-view, a predetermined value is used. However, the focus control unit 350 may receive an operator's desired value via the imaging condition input unit 210. In this case, a configuration may be adopted in which the monitor 213 of the imaging condition input unit 210 displays the projection position movement amount obtained by accumulating the gap width (Δch1) in FIG. 16 for each view, and in which an operator inputs the gap width (Δch1') which achieves (N−½) while referring to the displayed movement amount.

Next, in Step 1203 in FIG. 15, the focus control unit 350 calculates the focal movement distance ΔS1 (ΔS1-2, ΔS1-3, ΔS1-4 . . . ) of the focal position for each view-to-view which is necessary for realizing the desired gap width (Δch1') set for each view-to-view in Step 1202 with regard to the point within the first region 14. Each ΔS1 is calculated similarly to the first embodiment.

In Step 1204, the focus control unit 350 instructs the integrated controller 345 the focal movement distance ΔS1 (ΔS1-2, ΔS1-3, ΔS1-4 . . . ) calculated in Step 1203.

In this manner, the focal position is moved for each view, and the projection position of the point within the first region 14 is moved (interlaced) as far as (N−½) times the channel width 24, thereby enabling the imaging.

In FIG. 16, a change (Δch1'-Δch1) in the movement amount which is caused by the presence or absence of the focal movement, and the movement amount of the projection position which is obtained by accumulating the set desired gap width (Δch1') for each view are also illustrated as a reference.

Other configurations of the X-ray CT device according to the fifth embodiment are the same as those according to the first embodiment, and thus, description thereof will be omitted.

According to the fifth embodiment, the focus control unit 350 calculates the focal movement distance ΔS1 for each view-to-view, and sets the focal position. Therefore, spatial resolution (resolution) can be improved in a annulus-shaped peripheral region that is the vicinity of the distance R from the rotation center O.

The fifth embodiment is preferably adopted in a case where the gap width (Δch) of the projection position in case of no focal movement is slightly shifted from 1ch (for example, 1.1ch) as illustrated in FIG. 16.

In addition, the fifth embodiment may adopt a configuration in which the focus control unit 350 calculates the focal movement distance ΔS1 (ΔS1-2, ΔS1-3, ΔS1-4 . . . ) for each view-to-view by performing calculation in advance in a flow in FIG. 15 and stores the focal movement distance ΔS1 (ΔS1-2, ΔS1-3, ΔS1-4 . . . ) in the memory. Then, in Step 62 in FIG. 5(b), the focus control unit 350 can read the focal movement distance ΔS1 (ΔS1-2, ΔS1-3, ΔS1-4 . . . ) stored in the memory of the focus control unit 350, and can instruct the integrated controller 345 the focal movement distance ΔS1 (ΔS1-2, ΔS1-3, ΔS1-4 . . . ). In addition, in Step 902 in FIG. 15, in a case where the desired gap width (Δch1') is received from an operator, a configuration can also be adopted in which each ΔS (ΔS1-2, ΔS1-3, ΔS1-4 . . . ) is obtained for a value of Δch1' between multiple receivable types of view and an operator selects one from sets of the multiple types of Δch1'.

Sixth Embodiment

An X-ray CT device according to a sixth embodiment will be described with reference to FIG. 17.

The sixth embodiment adopts a configuration which is the same as that according to the fifth embodiment. In contrast, in Step 1202, as the gap width (Δch1') of the projection position between views, the focus control unit 350 combines the adjacent views with each other, and sets a value which satisfies (N−½) times (where N=any one of 1, 2, 3 . . . ) for only view-to-view within the combination.

For example, as illustrated in FIG. 17, the first and second views are combined with each other, and the third and fourth views are combined with each other, thereby setting the value which satisfies (N−½) times as Δch1' within these combinations. Specifically, Δch'=−1.5ch is set between the first and second views, and Δch1'=−1.5ch is set between the third and fourth views. On the other hand, a value which does not satisfy (N−½) times is set between the second and third views. Specifically, Δch1'=0.7ch is set therebetween.

In this manner, as in the fifth embodiment, all of the views are not interlaced with each other. However, the interlaced relationship is ensured between at least the adjacent views. Accordingly, it is possible to obtain an advantageous effect that resolution is improved to a fixed level or higher. In addition, it is possible to optionally set the focal movement amount between the combination and the combination. Therefore, it is possible to employ a method of setting Δch1' in which the focal movement amount is reduced.

Other configurations of the X-ray CT device according to the sixth embodiment are the same as those according to the fifth embodiment, and thus, description thereof will be omitted.

Seventh Embodiment

An X-ray CT device according to a seventh embodiment will be described with reference to FIG. 18.

According to the seventh embodiment, the adjacent views are combined with each other similarly to the sixth embodiment, and Δch1' is set so that a movement amount change (Δch1'-Δch1) caused by the focal movement is 0.5ch between views within the combination as illustrated in FIG. 18. In addition, the movement amount change (Δch1'-Δch1) caused by the focal movement is set to zero between a view of the combination and a view of the combination.

Eighth Embodiment

Figure 19:
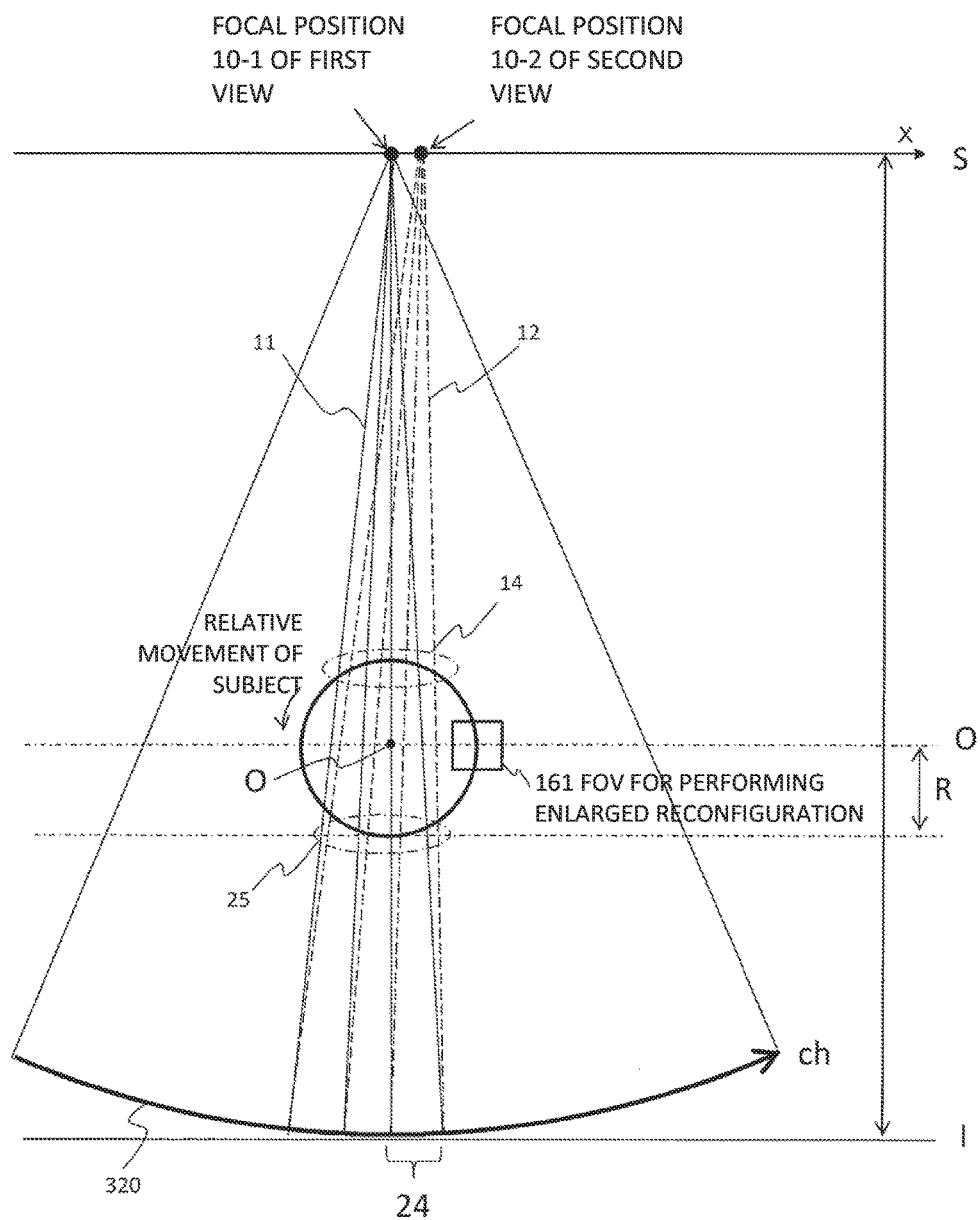
FIG. 19 is a view for describing an example of setting a distance between a center of an FOV for enlarged reconstruction and the rotation center O to a distance R according to an eighth embodiment.

An X-ray CT device according to an eighth embodiment will be described with reference to FIG. 19.

The X-ray CT device according to the eighth embodiment adopts a configuration which is the same as that according to the first embodiment. In contrast, in Step 804 in FIG. 6, the image generation unit 400 sets a FOV for performing enlarged reconstruction 161 in a local region, and obtains an enlarged CT image for the FOV for performing enlarged reconstruction 161 by using an enlarged reconstruction method. Therefore, the FOV for performing enlarged reconstruction 161 is set at a predetermined position as illustrated in FIG. 19 or a position input by an operator. Here, FIG. 19 illustrates a coordinate system fixed to the X-ray detector 320 of the rotary plate 332.

According to the eighth embodiment, a distance between the rotation center O and the center of the FOV for performing enlarged reconstruction 161 is used as the distance R for setting the rotation center O in the first region 14 and the second region 25. In Step 62 in FIG. 5(b), calculation of Expressions (1) and (2) is performed using the distance R. In this manner, the enlarged reconstruction method improves resolution of the FOV for performing enlarged reconstruction 161.

Ninth Embodiment

Figure 20:
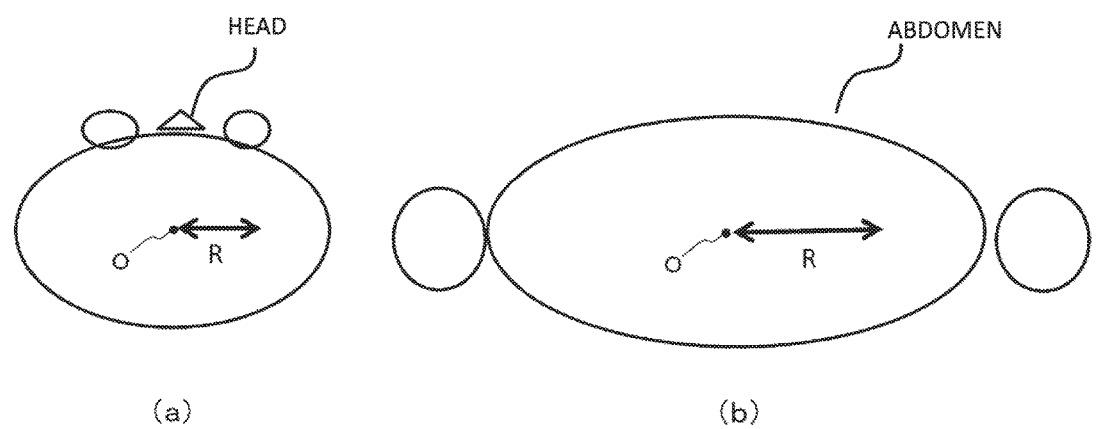

An X-ray CT device according to a ninth embodiment will be described with reference to FIGS. 20(a) and 20(b).

The X-ray CT device according to the ninth embodiment adopts a configuration which is the same as that according to the first embodiment. In contrast, as illustrated in FIGS. 20(a) and 20(b), an operator sets a head, an abdomen, etc. as an imaging target, and determines a value of the distance R in advance for each selectable site in an imaging condition setting step 350 so as to store the value in the memory inside the focus control unit 350. In a case where the operator selects the imaging target in the imaging condition setting step 601 in FIG. 5(a), the focus control unit 350 reads and uses the value of the distance R corresponding to the selected imaging site as the distance R from the rotation center O in the first region 14 and the second region 25, from the incorporated memory. In Step 62 in FIG. 5(b), calculation of Expressions (1) and (2) is performed using the distance R.

In this manner, it is possible to improve resolution in a region (first region 14) of the distance R which is suitable for a site of the imaging target.

Tenth Embodiment

Figure 21:
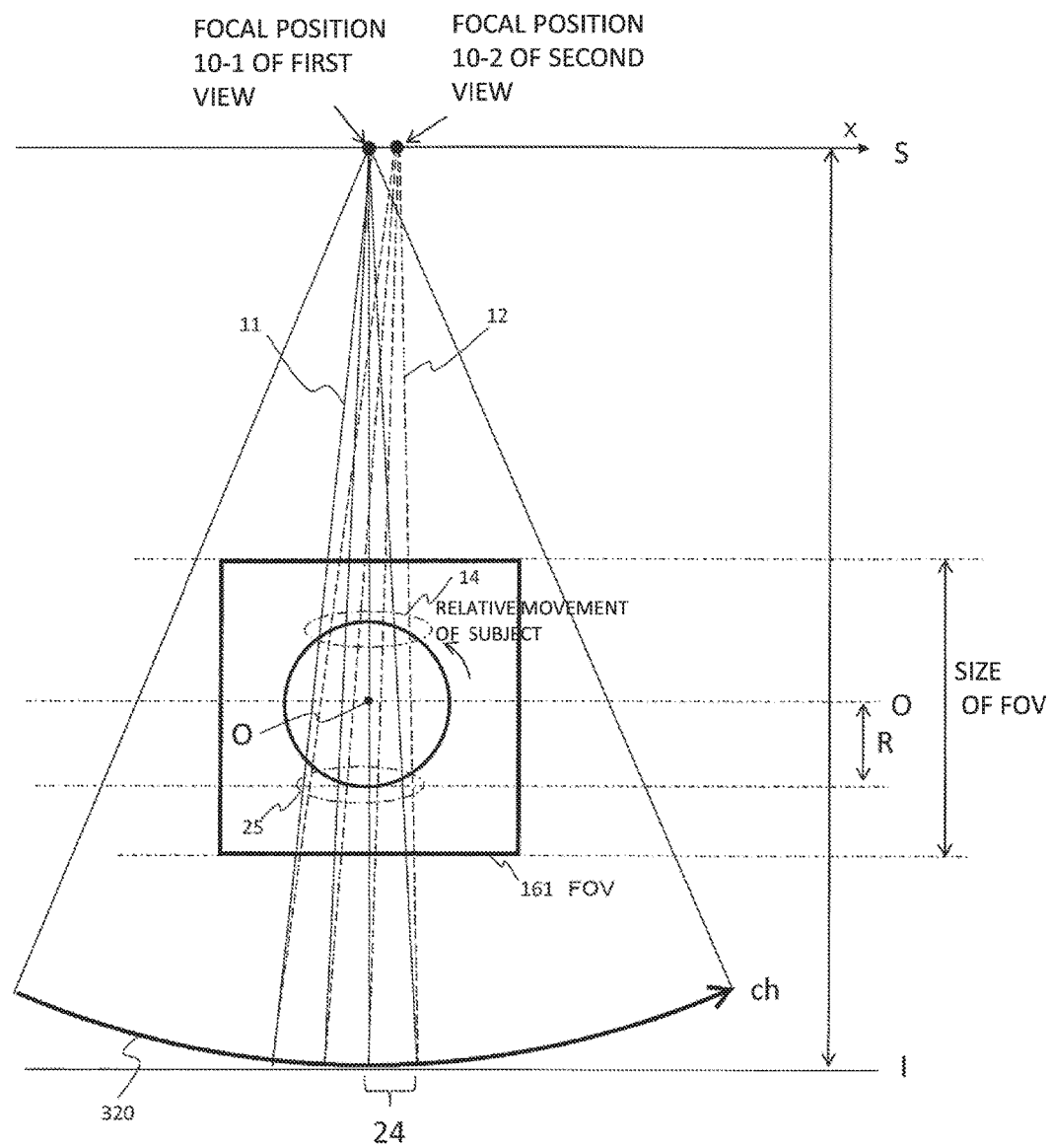
FIG. 21 is a view for describing an example of setting the distance R in accordance with a size of the FOV according to a tenth embodiment.

An X-ray CT device according to a tenth embodiment will be described with reference to FIG. 21.

The X-ray CT device according to the tenth embodiment adopts a configuration which is the same as that according to the first embodiment. In contrast, the focus control unit 350 sets the distance R in accordance with a size of an imaging target's FOV which is set by an operator in the imaging condition setting step 601 in FIG. 5(a).

For example, the focus control unit 350 calculates R by using predetermined Expression (10).

$$R = FOV \times k \qquad (10)$$

where k is a predetermined constant.

In Step 62 in FIG. 5(b), the focus control unit 350 performs calculation of Expressions (1) and (2) by using the calculated distance R.

In this manner, it is possible to improve resolution in a region (first region 14) of the distance R which is suitable for a size of the imaging target's FOV.

Eleventh Embodiment

Figure 22:
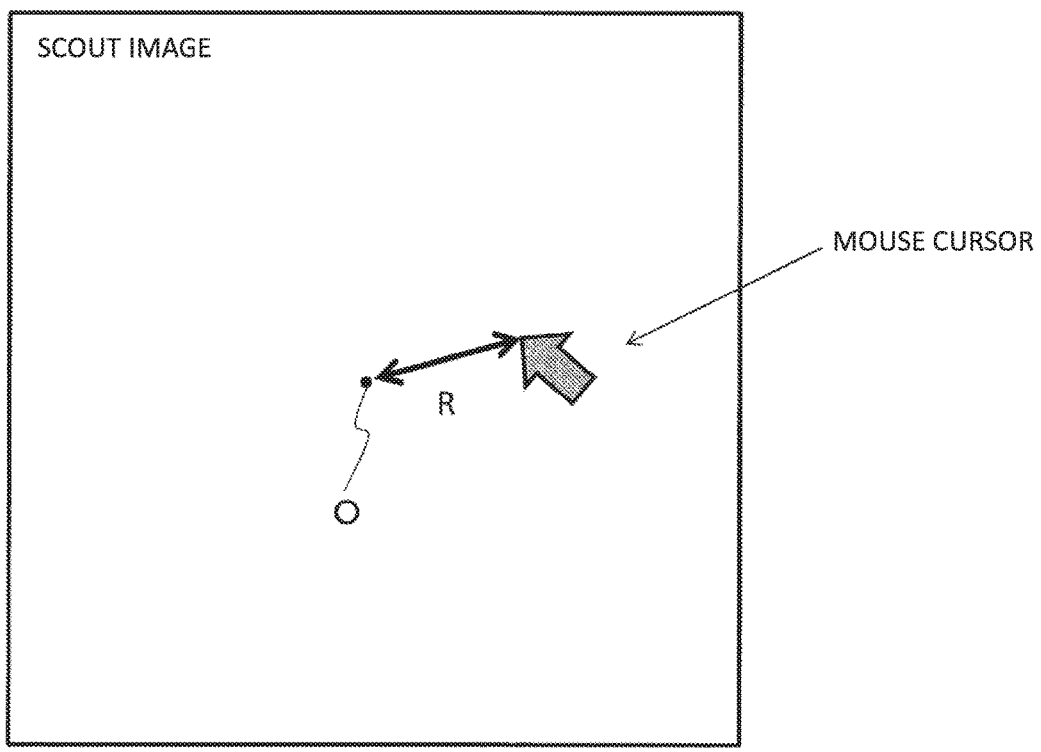
FIG. 22 is a view for describing an example of setting the distance R in accordance with a size displayed on a screen by an operator according to an eleventh embodiment.

An X-ray CT device according to an eleventh embodiment will be described with reference to FIG. 22.

The X-ray CT device according to the eleventh embodiment adopts a configuration which is the same as that according to the first embodiment. In contrast, a configuration is adopted in which in the imaging condition setting step 601 in FIG. 5(a), as illustrated in FIG. 22, an operator sets the distance R by using a mouse 211 as illustrated in FIG. 22 on a screen of the monitor 213 of the imaging condition input unit 210. The focus control unit 350 receives the distance R set by the operator via the imaging condition setting unit 210, and performs calculation of Expressions (1) and (2) in Step 62 in FIG. 5(b).

In this manner, it is possible to improve resolution in a region (first region 14) of the distance R which is desired by the operator.

Twelfth Embodiment

Figure 23:
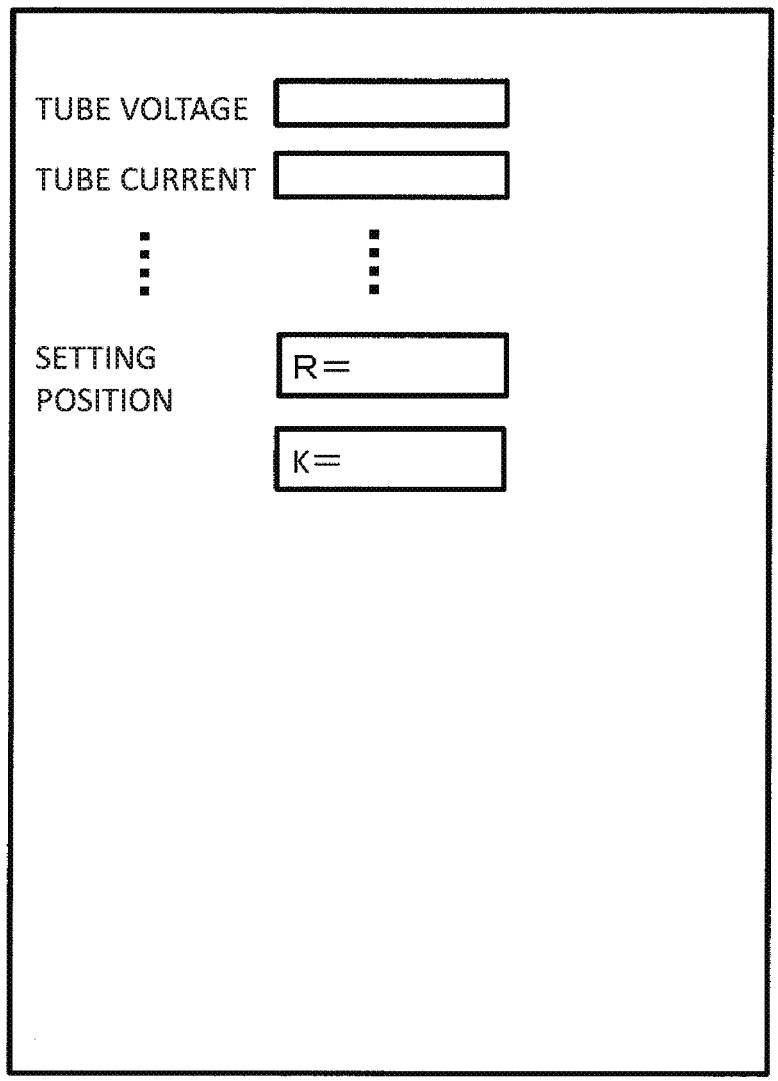
FIG. 23 is a view for describing an example of setting the distance R, based on a value input onto an imaging condition input screen by an operator according to a twelfth embodiment.

An X-ray CT device according to a twelfth embodiment will be described with reference to FIG. 23.

The X-ray CT device according to the twelfth embodiment adopts a configuration which is the same as that according to the first embodiment. In contrast, in the imaging condition setting step 601 in FIG. 5(a), as illustrated in FIG. 23, a screen to which an operator inputs an imaging condition such as a tube voltage and a tube current also includes an input region of the distance R. In addition, the screen may include a region to which a coefficient k according to the seventh embodiment is input. The operator can set an imaging condition in such a way that a numerical value or selecting a numerical value of the distance R or the coefficient k is input by using the keyboard 211 or the mouse 212 via the imaging condition input unit 210. The focus control unit 350 receives the distance R set by the operator via the imaging condition setting unit 210, and performs calculation of Expressions (1) and (2) in Step 62 in FIG. 5(b). In a case where the coefficient k is received, as in the tenth embodiment, the focus control unit 350 uses k, the FOV input as the imaging condition after calculating R from Expression (10).

In this manner, it is possible to improve resolution in a region (first region 14) of the distance R which is desired by the operator.

Thirteenth Embodiment

Figure 24:
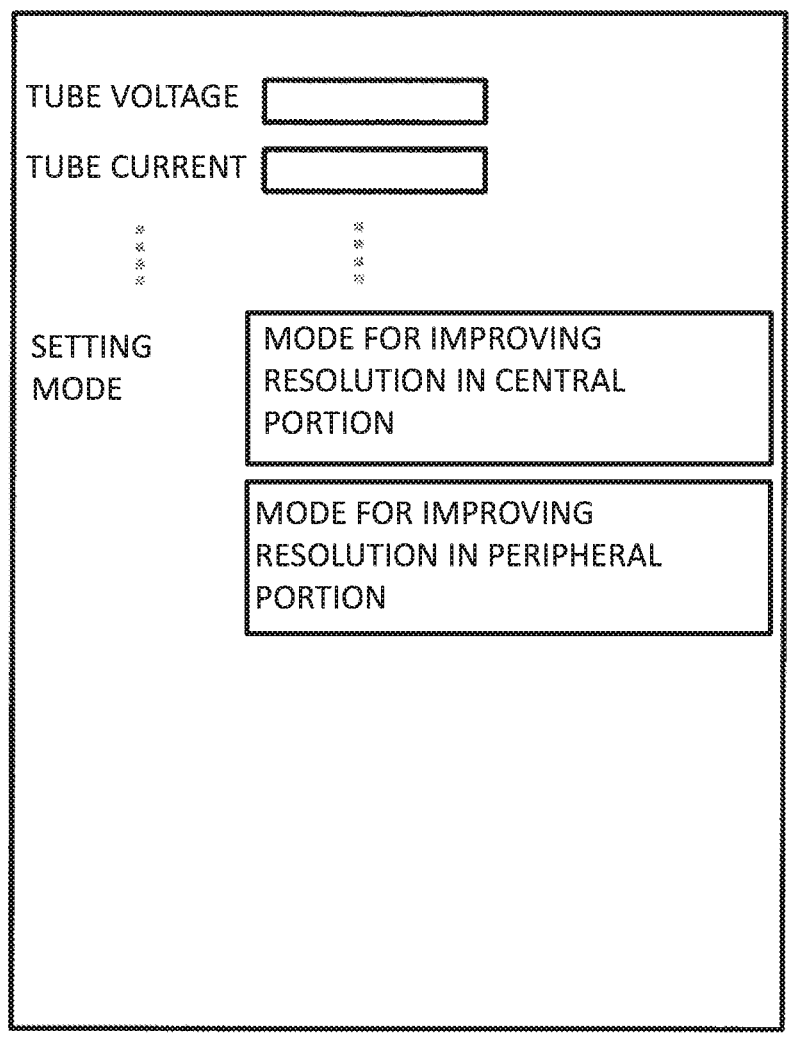
FIG. 24 is a view for describing an example of setting the distance R, based on a setting mode selected on an imaging condition input screen by an operator according to a thirteenth embodiment.

An X-ray CT device according to a thirteenth embodiment will be described with reference to FIG. 24.

The X-ray CT device according to the thirteenth embodiment adopts a configuration which is the same as that according to the first embodiment. In contrast, in the imaging condition setting step 601 in FIG. 5 (*a*), as illustrated in FIG. 24, a selection region of a setting mode for setting a region whose resolution is to be improved on an image is included on a screen to which an operator inputs an imaging condition such as a tube voltage and a tube current.

For example, "improving resolution in a central portion" and "improving resolution in a peripheral portion" are prepared in the setting mode. In a case where the operator selects "improving resolution in a central portion", for example, the focus control unit 350 sets k=0.1, as the coefficient k according to the tenth embodiment. In a case where the operator selects "improving resolution in a peripheral portion", for example, the focus control unit 350 sets k=0.8, as the coefficient k. In this manner, as in the tenth embodiment, the focus control unit 350 uses the coefficient k in calculation of Expressions (1) and (2) after calculating R from Expression (10). In this manner, it is possible to improve resolution in a region desired by the operator.

Other configurations according to the above-described eighth to thirteenth embodiments are the same as those according to the first embodiment, and thus, description thereof will be omitted. In addition, in the eighth to thirteenth embodiments, an operation of the focus control unit 350 can employ an operation according to the second to seventh embodiments, as a matter of course.

REFERENCE SIGNS LIST

100: X-RAY CT DEVICE,
200: INPUT UNIT,
210: IMAGING CONDITION INPUT UNIT,
211: KEYBOARD,
212: MOUSE,
213: MONITOR,
300: IMAGING UNIT,
310: X-RAY GENERATION UNIT,
311: X-RAY TUBE,
320: X-RAY DETECTION UNIT,
321: CHANNEL,
330: GANTRY,
331: OPENING PORTION,
332: ROTARY PLATE,
340: IMAGING CONTROL UNIT,
341: X-RAY CONTROLLER,
342: GANTRY CONTROLLER,
343: TABLE CONTROLLER,
344: DETECTOR CONTROLLER,
345: INTEGRATED CONTROLLER,
400: IMAGE GENERATION UNIT,
410: SIGNAL ACQUISITION UNIT,
411: DATA ACQUISITION SYSTEM, DAS,
420: DATA PROCESSING UNIT,
421: CENTRAL PROCESSING UNIT,
422: MEMORY,
423: HDD DEVICE,
440: IMAGE DISPLAY UNIT,
441: IMAGE DISPLAY MONITOR,
500: SUBJECT,
501: SUBJECT MOUNTING TABLE

The invention claimed is:

1. An X-ray CT device comprising:
   an X-ray tube provided with capability to move an X-ray focal point;
   an X-ray detector;
   a table which disposes a subject between the X-ray tube and the X-ray detector;
   a rotary plate that is mounted with the X-ray tube and the X-ray detector so as to rotate the X-ray tube and the X-ray detector around the subject;
   a reconstruction processing unit that reconstructs an image by incorporating a detection result of the X-ray detector with regard to multiple views corresponding to a rotation angle of the rotary plate; and
   a focus control unit that sets a position of the X-ray focal point of the X-ray tube for each of the views,
   wherein the X-ray detector includes multiple channels which are arrayed along a rotation direction of the rotary plate,
   wherein;
   first X-ray trajectories are X-ray trajectories reaching the X-ray detector from the X-ray focal point in a predetermined first view out of the multiple views,
   second X-ray trajectory are X-ray trajectories reaching the X-ray detector from the X-ray focal point in a second view adjacent to the first view,
   wherein;
   the focus control unit sets a position of each X-ray focal point of the first view and the second view so that a gap width of projection positions on the X-ray detector of the first X-ray trajectory and the second X-ray trajectory which respectively pass through the same point of the subject within a predetermined region different from a rotation center of the rotary plate is closer to $(N-\frac{1}{2})$ times (N=any one of 1, 2, 3, . . . ) of a width of the channel of the X-ray detector, compared to a gap width of projection positions on the X-ray detector of the first X-ray trajectory and the second X-ray trajectory which respectively pass through the rotation center of the rotary plate.

2. The x-ray CT device according to claim 1,
wherein the focus control unit sets a position of the X-ray focal point of the second view so that both of a gap width of the projection positions on the X-ray detector of the first X-ray trajectory and the second X-ray trajectory which respectively pass through the same point of the subject within a predetermined first region close to the X-ray focal point from the rotation center and a gap width of the projection positions on the X-ray detector of the first X-ray trajectory and the second X-ray trajectory which respectively pass through the same point of the subject within a predetermined second region close to the X-ray detector from the rotation center is closer to $(N-\frac{1}{2})$ times (N=any one of 1, 2, 3, . . . ) of the channel width, compared to the gap width of projection positions on the X-ray detector of the first X-ray trajectory and the second X-ray trajectory which respectively pass through the rotation center.

3. The X-ray CT device according to claim 2,
wherein the first region and the second region are located on a line reaching the X-ray detector from the X-ray tube through the rotation center.

4. The X-ray CT device according to claim 1,
wherein in the X-ray focal point of the first view and the X-ray focal point of the second view, positions in a coordinate system which are fixed to the X-ray detector of the rotary plate do not overlap each other.

5. The X-ray CT device according to claim 1,
wherein the focus control unit sets each X-ray focal point of the multiple views so that any one of the multiple views satisfies a relationship of the gap width of the projection positions on the X-ray detector of the first and second views with respect to an adjacent view.

6. The X-ray CT device according to claim 1,
wherein the focus control unit alternately sets a first X-ray focal point and a second X-ray focal point in the order of view numbers with respect to the multiple views.

7. The X-ray CT device according to claim 1,
wherein the focus control unit sets a position of the X-ray focal point for each of the views.

8. The X-ray CT device according to claim 1,
wherein the reconstruction processing unit is configured to set a FOV for enlarged reconstruction in a local region, and to obtain an enlarged CT image with regard to the FOV for enlarged reconstruction by using an enlarged reconstruction method, and
wherein as the predetermined region, the focus control unit uses a region located close to the X-ray focal point from the rotation center at a distance which is equal to a distance between the rotation center and the FOV for enlarged reconstruction.

9. The X-ray CT device according to claim 1, further comprising:
a reception unit that receives settings of a portion of the subject to be imaged,
wherein as the predetermined region, the focus control unit sets a region located close to the X-ray focal point from the rotation center, as far as a distance which is determined in advance for each portion received by the reception unit.

10. The X-ray CT device according to claim 1,
wherein as the predetermined region, the focus control unit sets a region shifted toward the X-ray focal point from the rotation center, as far as a distance corresponding to a size of a FOV in which the reconstruction processing unit reconstructs an image.

11. An imaging method for an X-ray CT image in which a position of an X-ray focal point of an X-ray tube is set for each view by the X-ray tube and an X-ray detector being mounted on a rotary plate while the X-ray tube and the X-ray detector are rotated around a subject, the imaging method comprising:
wherein first X-ray trajectory are X-ray trajectories reaching the X-ray detector from the X-ray focal point in a predetermined first view from among the multiple views, second X-ray trajectories are X-ray trajectories reaching the X-ray detector from the X-ray focal point in a second view adjacent to the first view;
setting a position of each X-ray focal point of the first view and the second view so that a gap width of projection positions on the X-ray detector of the first X-ray trajectory and the second X-ray trajectory which respectively pass through the same point of the subject within a predetermined region different from a rotation center of the rotary plate is closer to $(N-\frac{1}{2})$ times (N=any one of 1, 2, 3, ... ) of a channel width of the X-ray detector, compared to a gap width of projection positions on the X-ray detector of the first X-ray trajectory and the second X-ray trajectory which respectively pass through the rotation center of the rotary plate.

* * * * *